(12) United States Patent
Szulc et al.

(10) Patent No.: US 12,390,490 B2
(45) Date of Patent: Aug. 19, 2025

US012390490B2

(54) SPHINGOLIPID-BASED SELENIUM COMPOUNDS, METHODS FOR THEIR PREPARATION, AND PHARMACEUTICAL USES THEREOF, INCLUDING AS ANTITUMOR AGENTS

(71) Applicant: MUSC FOUNDATION FOR RESEARCH DEVELOPMENT, Charleston, SC (US)

(72) Inventors: Zdzislaw M. Szulc, Charleston, SC (US); Besim Ogretmen, Mount Pleasant, SC (US); Natalia Oleinik, Charleston, SC (US)

(73) Assignee: MUSC FOUNDATION FOR RESEARCH DEVELOPMENT

( * ) Notice: Subject to any disclaimer, the term of this patent is extended or adjusted under 35 U.S.C. 154(b) by 623 days.

(21) Appl. No.: 17/637,129

(22) PCT Filed: Aug. 28, 2020

(86) PCT No.: PCT/US2020/048430
§ 371 (c)(1),
(2) Date: Feb. 22, 2022

(87) PCT Pub. No.: WO2021/041825
PCT Pub. Date: Mar. 4, 2021

(65) Prior Publication Data
US 2022/0288109 A1 Sep. 15, 2022

Related U.S. Application Data

(60) Provisional application No. 62/893,854, filed on Aug. 30, 2019.

(51) Int. Cl.
*A61K 33/04* (2006.01)
*A61K 31/4425* (2006.01)
*A61P 35/00* (2006.01)

(52) U.S. Cl.
CPC .......... *A61K 33/04* (2013.01); *A61K 31/4425* (2013.01); *A61P 35/00* (2018.01)

(58) Field of Classification Search
CPC ...... A61K 33/04; A61K 31/4425; A61P 35/00
See application file for complete search history.

(56) References Cited

U.S. PATENT DOCUMENTS 8,093,393 B2   1/2012   Bielawska et al.
2019/0125787 A1   5/2019   Fuchs

FOREIGN PATENT DOCUMENTS

WO   2007/136635 A1   11/2007
WO   2018/015776 A1   1/2018
WO   2019/051312 A1   3/2019

OTHER PUBLICATIONS

The extended European Search Report and Written Opinion, mailed on Sep. 7, 2023, in the corresponding European Appl. No. 20858846.7.
The International Search Report and Written Opinion, mailed on Dec. 2, 2020, in the corresponding PCT Appl. No. PCT/US2020/048430.

*Primary Examiner* — Robert A Wax
*Assistant Examiner* — Olga V. Tcherkasskaya

(57) ABSTRACT

Ionic conjugates of selenite anions and cationic ceramide analogs are described. For instance, conjugates can comprise ionic conjugates of selenite anions and pyridimin-substituted ceramide analogs. Also described is the use of the ionic conjugates in treating cancer, such as head and neck cancer and brain cancer.

14 Claims, 28 Drawing Sheets

SPHINGOLIPID-BASED SELENIUM COMPOUNDS, METHODS FOR THEIR PREPARATION, AND PHARMACEUTICAL USES THEREOF, INCLUDING AS ANTITUMOR AGENTS

CROSS-REFERENCE TO RELATED APPLICATIONS

This application is a National Stage Application of PCT/US2020/048430 filed on Aug. 28, 2020, which claims benefit of U.S. Provisional Patent Application Ser. No. 62/893,854, filed Aug. 30, 2019. Each of prior mentioned applications is herein incorporated by reference in its entirety.

GOVERNMENT INTEREST

This invention was made with government support under Grant No. 5P01 CA203628 awarded by the National Institutes of Health and the National Cancer Institute. The government has certain rights in the invention.

TECHNICAL FIELD

The presently disclosed subject matter relates to compositions comprising ionic conjugates comprising selenite anions and cationic ceramide analogs, such as pyridinium-substituted ceramide analogs. The presently disclosed subject matter further relates to the treatment of cancer, such as brain cancer and head and neck cancers, using the ionic conjugates.

ABBREVIATIONS

- %=percent (or percentage)
- ° C.=degrees Celsius
- μM=micromolar
- ACO2=aconitase 2
- CerS1=Ceramide Synthase 1
- Dnm1=dynamin 1
- GB=glioblastoma
- h=hours
- HA=human astrocyte
- HNSCC=head and neck small cell carcinoma
- kg=kilogram
- LC3 (or LC3B)=microtubule-associated proteins 1A/1B light chain 3 (or light chain 3)
- mg=milligram
- min=minutes
- ml=milliliter
- mm³=cubic millimeters
- mM=millimolar
- MRI=magnetic resonance imaging
- MTD=maximum tolerated dose
- MTT=3-(4,5-dimethylthiazol-2-yl)-2,5-dimethyltetrazolium bromide
- NMR=nuclear magnetic resonance
- pmol=picomoles
- RP=reverse phase
- SCID=severe combined immunodeficiency
- Se=selenium
- shRNA=short hairpin RNA
- Se=selenium
- SoSe=sodium selenite
- SPL-BSe=sphingolipid-based selenium
- TLC=thin layer chromatography

BACKGROUND

Autophagy is a process by which cells self-digest cytoplasmic components that are damaged or unnecessary. In this process, the unnecessary/damaged components are enveloped by a phagophore consisting of a lipid bilayer membrane called an autophagosome and decomposed after fusion with a lysosome. Autophagy can promote cell survival during starvation or can progress to cell death (lethal autophagy). Selective degradation of mitochondria by autophagy is called mitophagy. Degradation of mitochondria can limit cellular energy production and inhibit the synthesis of macromolecules, such as nucleotides and amino acids, leading to cell death (lethal mitophagy).

Compounds that stimulate the lethal mitophagy pathway preferentially in cancer cells are of interest in the development of anticancer treatments. Accordingly, there is an ongoing need for additional compounds and methods for treating cancer, particularly those that can stimulate lethal mitophagy in cancer cells.

SUMMARY

In some embodiments, the presently disclosed subject matter provides a composition comprising an ionic conjugate comprising a selenite anion and a cationic ceramide analog. In some embodiments, the ionic conjugate has a structure of Formula (I):

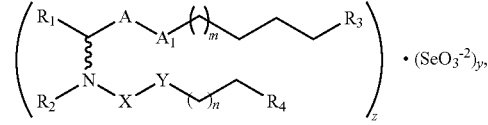

wherein: n is an integer from 3 to 21; m is an integer from 1 to 5; z is 1 or 2; y is an integer of I or more; A is selected from $-CH_2-$, $-CH(OH)-$, and $-C(=O)-$; $A_1$ is selected from $-CH=CH-(CH_2)_4-CH_2-$, $-(CH_2)_7-$, and $-C\equiv C-(CH_2)_4-CH_2-$; X is selected from $-C(=O)-$, $-C(=S)-$, $-C(=NH)-$, and $-CH(R_2)-$; Y is selected from $-N(R_2)-$, $-O-$, $-S-$, $-CH(OH)-$, $-CH(R_6)$, and $-CH_2-$; $R_1$ is selected from $-CH_3$, $-CH_2SH$, $-CH_2NH_2$, $-CH_2NHR_6$, $-CH_2NR_6(R_7)-$, and $-CH_2OH$; $R_2$ is selected from $-H$ and $C_1$-$C_6$ alkyl; $R_3$ is selected from $-H$, $-NHR_6$, $-NR_6(R_7)$, $-^+NHR_6(R_7)$, $-^+NR_6(R_7)_2$, and N-heterocycle; $R_4$ is selected from $-H$, $-NHR_6$, $-NR_6(R_7)$, $-^+NHR_6(R_7)$, $-^+NR_6(R_7)_2$, and N-heterocycle; and each $R_6$ and $R_7$ is independently $-C_1$-$C_5$ alkyl, subject to the proviso that the ceramide analog component comprises at least one cationic moiety or at least one moiety capable of forming a cationic moiety in vivo.

In some embodiments, $A_1$ is $-CH=CH-(CH_2)_4-CH_2-$ and X is $-C(=O)-$, and the ionic conjugate of Formula (I) has a structure of Formula (II):

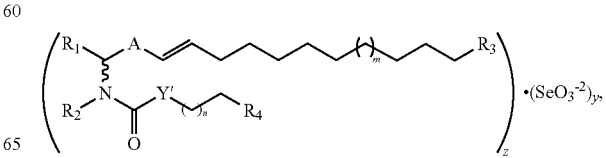

wherein: n is an integer from 3 to 21; m is an integer from 1 to 5; z is 1 or 2; y is an integer of 1 or more; A is —CH(OH)—; $R_1$ is —CH$_2$OH; $R_2$ is selected from —H and $C_1$-$C_6$ alkyl; $R_3$ is selected from —H, —NHR$_6$, —N(R$_6$)(R$_7$), —$^+$NHR$_6$(R$_7$), —$^+$NR$_6$(R$_7$)$_2$, and N-heterocycle; $R_4$ is selected from —H, —NHR$_6$, —N(R$_6$)(R$_4$), —$^+$NHR$_6$(R$_7$), —$^+$NR$_6$(R$_7$)$_2$, and N-heterocycle; and each $R_6$ and $R_7$ is independently —$C_1$-$C_5$ alkyl.

In some embodiments, $R_3$ and $R_4$ are each selected from —H and N-heterocycle, subject to the proviso that at least one of $R_3$ and $R_4$ is N-heterocycle, optionally wherein the N-heterocycle is pyridinium or substituted pyridinium. In some embodiments, $R_2$ is —H.

In some embodiments, Y is —CH$_2$—, and the ionic conjugate has a structure of Formula (IIIa):

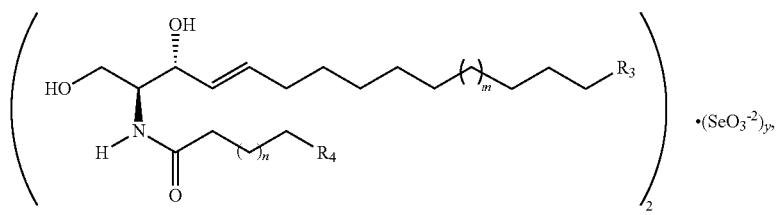

wherein: m is an integer between 1 and 5; n is an integer between 1 and 21; and $R_3$ and $R_4$ are each selected from —H and N-heterocycle, subject to the proviso that when Ra is —H, $R_4$ is N-heterocycle and when Ra is N-heterocycle, $R_4$ is —H. In some embodiments, m is 5, n is 13, $R_3$ is —H, and $R_4$ is pyridinium. In some embodiments, m is 1, n is 15, Ri is pyridinium, and $R_4$ is —H.

In some embodiments, Y' is —CH(OH)—, and the ionic conjugate has a structure of Formula (IIIb):

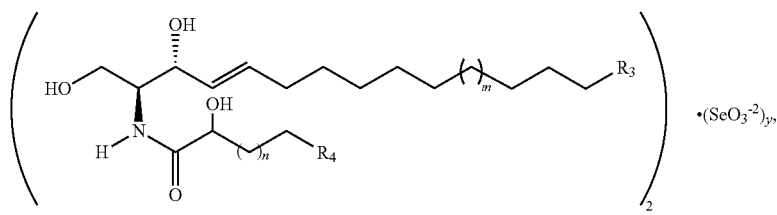 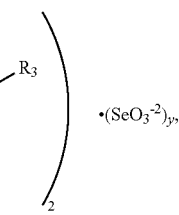

wherein: m is an integer between 1 and 5; n is an integer between 3 and 21; and $R_3$ and $R_4$ are each selected from —H and N-heterocycle, subject to the proviso that when $R_3$ is —H, $R_4$ is N-heterocycle and when $R_3$ is N-heterocycle, $R_4$ is —H. In some embodiments, n is an integer between 3 and 15, optionally wherein n is 13.

In some embodiments, the presently disclosed subject matter provides a pharmaceutical formulation comprising a pharmaceutically acceptable carrier and a composition comprising an ionic conjugate comprising a selenite anion and a cationic ceramide analog.

In some embodiments, the presently disclosed subject matter provides a method of treating cancer in a subject in need thereof, wherein the method comprises administering to the subject a composition comprising an ionic conjugate comprising a selenite anion and a cationic ceramide analog, or a pharmaceutical formulation thereof. In some embodiments, the administration of the ionic conjugate provides increased reduction in tumor cell load and/or reduced off-target selenite-related toxicity compared to treatment with a composition comprising selenite anion that is not provided as part of an ionic conjugate comprising a selenite anion and a cationic ceramide analog. In some embodiments, the administration of the ionic conjugate provides increased reduction in tumor cell load and/or reduced off-target toxicity compared to treatment with a non-conjugated mixture of a selenium-containing compound and a sphingolipid-based therapeutic agent. In some embodiments, the method provides effective use of a lower concentration of selenite anion than a method wherein the selenite anion is not administered as part of an ionic conjugate with a cationic ceramide analog.

In some embodiments, the cancer is a head and neck cancer or a brain cancer, optionally wherein the brain cancer is a glioblastoma.

It is an object of the presently disclosed subject matter to provide compositions comprising ionic conjugates comprising selenite anions and cationic ceramide analogs, pharmaceutical formulations thereof, and to provide methods of treating cancer using the compositions and formulations.

An object of the presently disclosed subject matter having been stated hereinabove, and which is achieved in whole or in part by the compositions and methods disclosed herein, other objects will become evident as the description proceeds when taken in connection with the accompanying Figures as best described herein below.

DETAILED DESCRIPTION

Figure 1A:
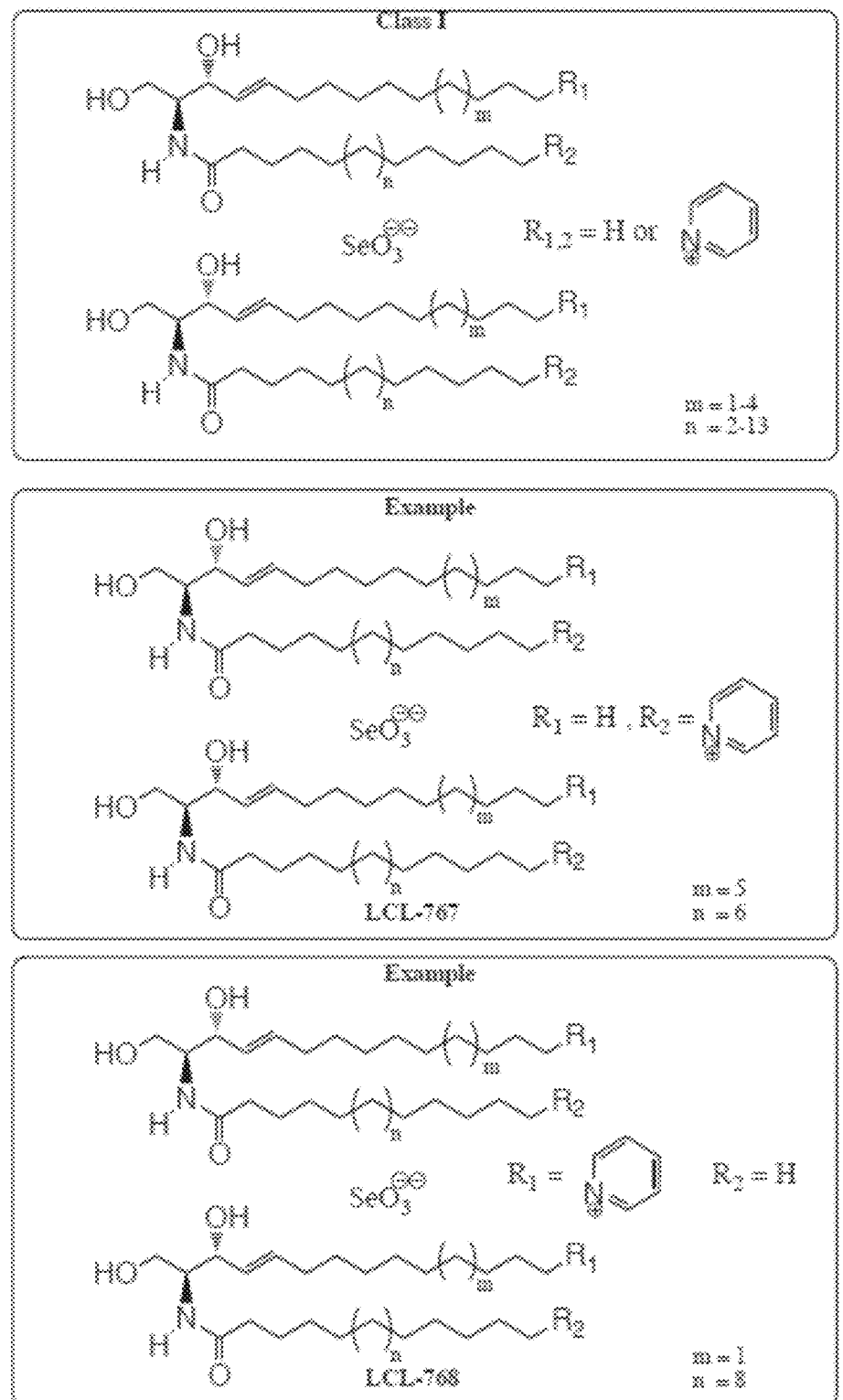
FIG. 1A is a schematic drawing showing the structures of exemplary Class I sphingolipid-based selenium (SPL-BSe) compounds, such as LCL-767 (middle) and LCL-768 (bottom), which comprise pyridinium-substituted ceramide-based selenite conjugated salts.
Figure 1B:
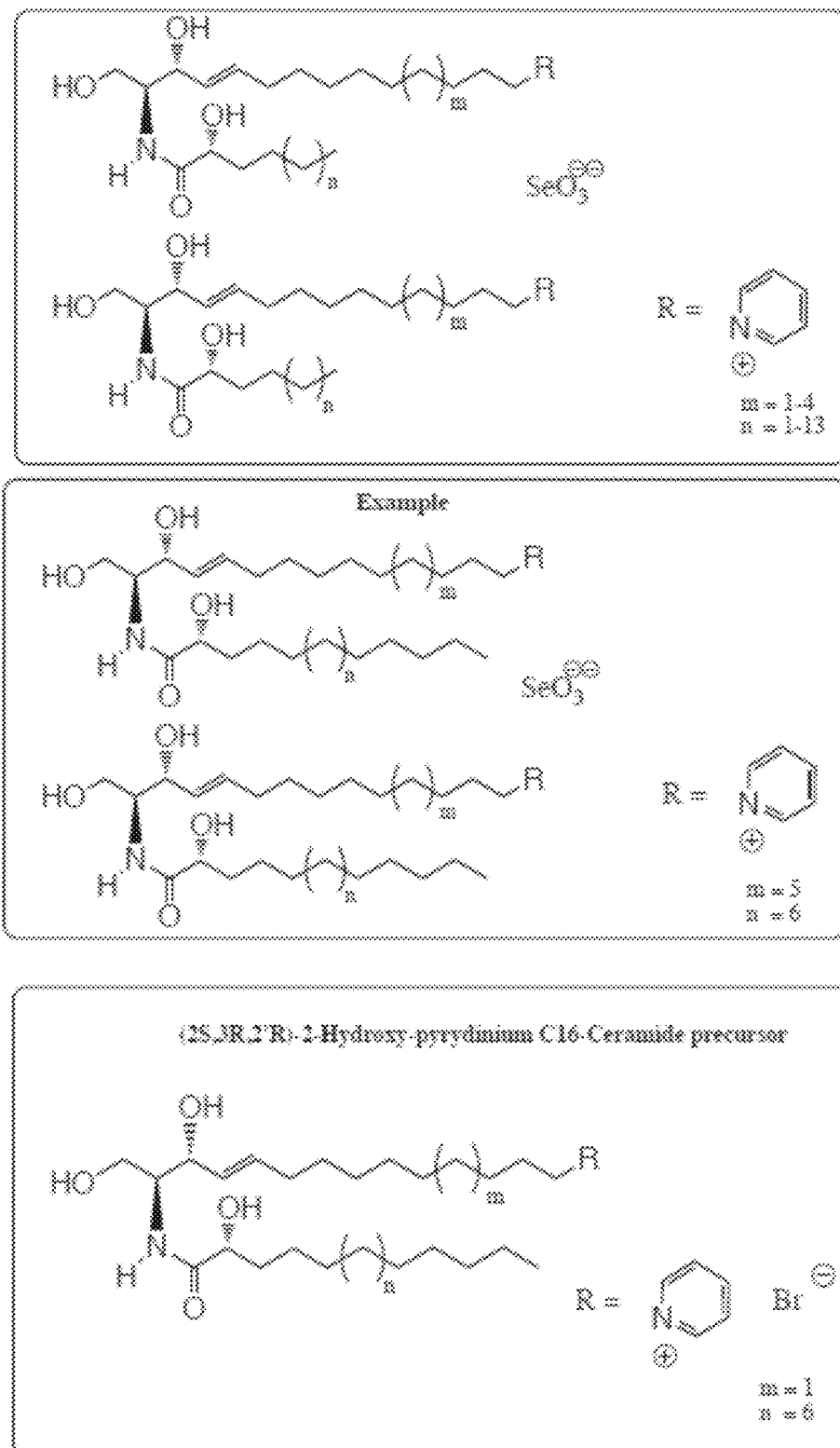
FIG. 1B is a schematic drawing showing the structures of additional exemplary Class I sphingolipid-based selenium (SPL-BSe) compounds which comprise pyridinium-substituted ceramide-based selenite conjugated salts. A representative example based on a (2S,3R,2'R)-2-hydroxyl-pyridinium C16-ceramide precursor (bottom) is shown in the middle of the figure.

The presently disclosed subject matter relates, in some embodiments, to sphingolipid-based selenium (SPL-BSe) compounds. In some embodiments, these compounds comprise a ceramide analog that includes an ionic moiety (e.g., a cationic moiety) incorporated (e.g., covalently incorporated) in its structure, wherein the ceramide analog is further conjugated (e.g., via ionic bonding) with selenite anion ($SeO_3^{-2}$). Thus, in some embodiments, the compounds are SPL-BSe ionic conjugates. Representative embodiments of the SPL-BSe ionic conjugates are shown in FIGS. 1A and 1B. Accordingly, the presently disclosed subject matter, in some embodiments, relates to the preparation of SPL-BSe ionic conjugates, the SPL-BSe ionic conjugates themselves, to pharmaceutical formulations comprising the SPL-BSe ionic conjugates, and to their use in treating disease, particularly to their use in treating cancer. Combinations of ceramide analogs and selenium compounds, such as the instantly disclosed SPL-BSe ionic conjugates, can induce cancer cell death in various solid tumors and leukemic cells via activation of mitochondrial damage and degradation in cancer cells.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

All references cited herein, including all patents, patent applications, database entries, and journal articles, are incorporated herein by reference in their entireties and for all purposes to the same extent as if each individual patent, patent application, database entry, or journal article was specifically and individually indicated to be incorporated by reference in its entirety for all purposes.

Unless otherwise defined, all technical and scientific terms used herein have the same meaning as commonly understood by one of ordinary skill in the art to which the presently described subject matter belongs. All publications, patent applications, patents, and other references mentioned herein are incorporated by reference in their entirety.

Throughout the specification and claims, a given chemical formula or name shall encompass all active optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a composition" or "a compound" includes a plurality of such compositions or compounds, and so forth.

Unless otherwise indicated, all numbers expressing quantities of size, reaction conditions, activity, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

A structure represented generally by a formula such as:

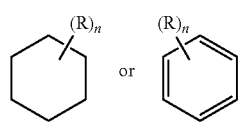

as used herein refers to a ring structure, for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure:

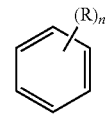

wherein n is an integer from 0 to 2 comprises compound groups including, but not limited to:

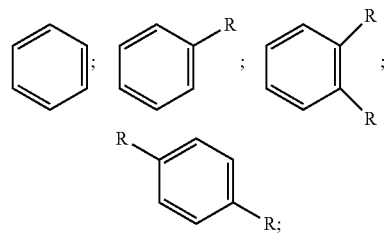

and the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The term "heterocycle" refers to a non-aromatic or aromatic, monocyclic or multicyclic ring system of about 3 to about 14 atoms, wherein at least one of the atoms is a heteroatom (e.g., oxygen, nitrogen, or sulfur). Heterocycles can be substituted or unsubstituted (i.e., with one or more alkyl or aryl group substituents. The term "N-heterocycle" refers to a heterocycle wherein at least one of the heteroatoms is a nitrogen atom. Examples of N-heterocycles include, but are not limited to, azetidine, pyrrolidine, pyrrole, pyrroline, piperidine, pyridine, piperazine, pyrazine, pyrimidine, pyridazine, morpholine, and thiazine.

"Aralkyl" refers to an aryl-alkyl- group wherein aryl and alkyl are as previously described, and included substituted aryl and substituted alkyl. Exemplary aralkyl groups include benzyl, phenylethyl, and naphthylmethyl.

As used herein, the term "acyl" refers to an organic carboxylic acid group wherein the —OH of the carboxyl group has been replaced with another substituent (i.e., as represented by RC(=O)—, wherein R is an alkyl, substituted alkyl, aralkyl, aryl or substituted aryl group as defined herein). As such, the term "acyl" specifically includes arylacyl groups, such as an acetylfuran and a phenacyl group. Specific examples of acyl groups include acetyl and benzoyl.

"N-acyl" refers to a group having the structure —N—C(=O)—R, wherein R is as defined for acyl. These groups can also be referred to as amides. Modified N-acyl groups include compounds wherein the oxygen of the N-acyl has been replaced by S or NH, as well as to compounds wherein the carbonyl group (i.e., the —C(=O)—) is attached to a second heteroatom in addition to the nitrogen. For example, the carbonyl can be attached to a second nitrogen atom to form a urea linkage (i.e., —NH—C(=O)—NH—R).

The term "amino" refers to the —NH$_2$, the —NHR, and the —NR$_2$ groups, wherein each R is independently alkyl, substituted alkyl, aryl, substituted aryl, or aralkyl, as well as to amino and ammonium functionalities in N-heterocycles (e.g., morpholine, etc). As used herein the term "amino" can also refer to substituents that provide quaternary ammonium cations, such as —$^+$NH$_3$, —$^+$NH(R)$_2$, and —$^+$N(R)$_3$ groups, wherein each R is independently alkyl, substituted alkyl, aryl, substituted aryl or aralkyl.

The term "ester" refers to a moiety comprising an —O—C(=O)—R group, wherein R can be alkyl, substituted alkyl, aralkyl, aryl, or substituted aryl. In some embodiments, the R group can include an amino substituent and the ester is an amino ester.

The term "amide" refers to a moiety comprising a —N(R')—C(=O)—R group, wherein R is selected from alkyl, substituted alkyl, aralkyl, aryl or substituted aryl and R' is H, alkyl, substituted alkyl, aralkyl, aryl, or substituted aryl.

The term "urea" as used herein can refer to a moiety comprising a —N(R')—C(=O)—N(R')— group, wherein each R' is independently H, alkyl, substituted alkyl, aralkyl, aryl, or substituted aryl.

The term "hydroxyl" refers to the —OH group.

When the term "independently selected" is used, the substituents being referred to (e.g., R groups, such as groups R$_1$ and R$_2$, or groups X and Y), can be identical or different. For example, both R$_1$ and R$_2$ can be substituted alkyls, or R$_1$ can be hydrogen and R$_2$ can be a substituted alkyl, and the like.

The terms "sphingolipid" and "glycosylceramide" can refer to a lipid comprising a sphingoid base backbone. Sphingoid base backbones include aliphatic amino alcohols, such as sphingosine (i.e., 2-amino-4-octadecene-1,3-diol).

The term "ceramide" can refer to an amide-containing compound formed from sphingosine having a fatty acid attached at the sphingosine amino group. In some embodiments, the ceramide is a naturally occurring molecule. Ceramides can be referred to as a "C$_n$-Cer", where n is the number of carbon atoms in the acyl group formed from the fatty acid. In some cases, the ceramide can include one or more double bonds in the fatty acid acyl group (e.g., C24:1-Cer, which is the ceramide with a 24 carbon fatty acid chain and one double bond).

II. Sphingolipid-Based Selenium Compounds and Compositions Thereof

In some embodiments, the presently disclosed subject matter provides a composition that comprises a combination of a ceramide or ceramide analog and a selenium-containing compound. The ceramide analog can be based on the structure of a natural ceramide derivatized to comprise, for example, a cationic moiety or a moiety that can be protonated to provide a cationic moiety under physiological conditions, such as an aliphatic or aromatic amino group. In some embodiments, the cationic group can be attached to an aliphatic chain of the ceramide structure. The ceramide analog can also comprise one or more additional structural variations as compared to a natural ceramide, such as, but not limited to, one or more alkyl group substituents attached to a carbon of the ceramide lipid chain or to the aliphatic chain of the amide (e.g., the substitution of the carbon adjacent to the carbonyl carbon of the amide group with a hydroxyl group), a reduced alkene bond, the replacement of the alkene bond with an alkyne bond, the replacement of a hydroxyl group with a hydrogen or an alkyl group, the replacement of the amide linkage with a thioamide, a urea, a carbamate, a ketone, or an ester, or the replacement of the amide bond carbonyl group with a methylene group or with a group comprising a carbon-nitrogen double bond. In some embodiments, the selenium compound is an inorganic selenium compound. In some embodiments, the selenium compound is selenite anion (SeO$_3^{-2}$).

In some embodiments, the composition comprises an ionic conjugate comprising a selenite anion as a first component and a ceramide or ceramide analog (e.g., a cationic ceramide analog) as a second component. In some embodiments, the conjugate comprises more than one first component and/or more than one second component. For example, in some embodiments, the ionic conjugate has a structure of Formula (I):

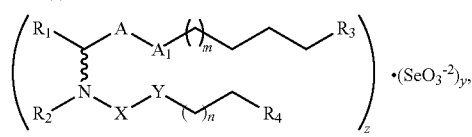

wherein: n is an integer from 3 to 21 (i.e., 3, 4, 5, 6, 7, 8, 9, 10, 11, 12, 13, 14, 15, 16, 17, 18, 19, 20, or 21); m is an integer from 1 to 5 (i.e., 1, 2, 3, 4, or 5); z is 1 or 2; y is an integer of 1 or more; A is selected from —CH$_2$—, —CH(OH)—, and —C(=O)—; A$_1$ is selected from —CH=CH—(CH$_2$)$_4$—CH$_2$—, —(CH$_2$)$_7$—, and —C≡C—(CH$_2$)$_4$—CH$_2$—; X is selected from —C(=O)—, —C(=S)—, —C(=NH)—, and —CH(R$_2$)—, Y is selected from —NR$_2$— (e.g., —NH—), —O—, —S—, —CH(OH)—, —CH(R$_6$)—, and —CH$_2$—; R$_1$ is selected from —CH$_3$, —CH$_2$SH, —CH$_2$NH$_2$, —CH$_2$NHR$_6$, —CH$_2$NR$_6$(R$_7$)—, and —CH$_2$OH; R$_2$ is selected from —H and C$_1$-C$_6$ alkyl; Ra is selected from —H, —NHR$_6$, —NR$_6$(R$_7$), —$^+$NHR$_6$(R$_7$), —$^+$NR$_6$(R$_7$)$_2$, and N-heterocycle; R$_4$ is selected from —H, —NHR$_6$, —NR$_6$(R$_7$), —$^+$NHR$_6$(R$_7$), —$^+$NR$_6$(R$_7$)$_2$, and N-heterocycle; and each R$_6$ and R$_7$ is independently a —C$_1$-C$_5$ alkyl group. Typically, the ceramide component (i.e., the portion of Formula (1) within the parentheses modified by "z") can include at least one or more cationic moieties (or moieties capable of forming cationic moieties in vivo). In some embodiments, the ceramide component can include one cationic moiety. In some embodiments, the ceramide component can include two cationic moieties. In some embodiments, A$_1$ is —CH=CH—(CH$_2$)$_4$—CH$_2$—. In some embodiments, X is —C(=O)—. In some embodiments, Y is —NH—, —CH(OH)—, or —CH$_2$—. In some embodiments, R$_2$ is —H.

In some embodiments, A$_1$ is —CH=CH—(CH$_2$)$_4$—CH$_2$— and X is —C(=O)—, and the ionic conjugate of Formula (I) has a structure of Formula (II):

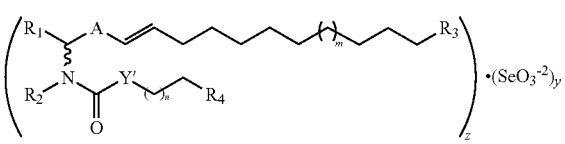

wherein: n is an integer from 3 to 21; m is an integer from 1 to 5; z is 1 or 2; y is an integer of 1 or more; A is —CH(OH)—; $R_1$ is —CH$_2$OH; Y' is selected from —CH$_2$—, —NH—, and —CH(OH)—; $R_2$ is selected from —H and $C_1$-$C_6$ alkyl; $R_3$ is selected from —H, —NHR$_6$, —N(R$_6$)(R$_7$), —$^+$NHR$_6$(R$_7$), —$^+$NR$_6$(R$_7$)$_2$, and N-heterocycle; $R_4$ is selected from —H, —NHR$_6$, —N(R$_6$)(R$_7$), —$^+$NHR$_6$(R$_7$), —$^+$NR$_6$(R$_7$)$_2$, and N-heterocycle; and each $R_6$ and $R_7$ is independently $C_1$-$C_5$ alkyl. In some embodiments, $R_3$ and $R_4$ are each selected from —H and N-heterocycle. In some embodiments, $R_2$ is —H.

In some embodiments, one or both of $R_3$ and $R_4$ are N-heterocycle (e.g., pyridinium) In some embodiments, the ionic conjugate has a structure of Formula (III):

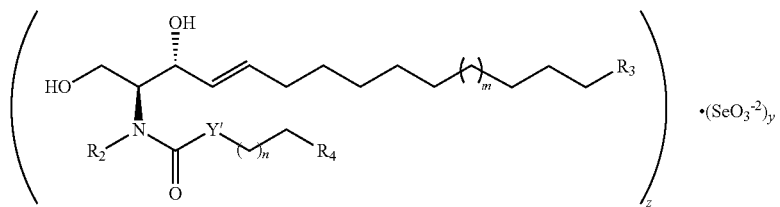

wherein: m is an integer between 1 and 5; n is an integer between 3 and 21; Y' is selected from Y' is selected from —CH$_2$—, —N(H)—, and CH(OH)—; and $R_3$ and $R_4$ are each selected from —H and N-heterocycle, subject to the proviso that when $R_3$ is —H, $R_4$ is N-heterocycle and when $R_3$ is N-heterocycle, $R_4$ is —H. In some embodiments, the N-heterocycle is pyridinium or substituted pyridinium. In some embodiments, the pyridinium-containing compounds of Formula (III) are also referred to herein as "Class I compounds."

In some embodiments, Y' is —CH$_2$— and $R_2$ is H; and the compound of Formula (III) is a compound of Formula (IIIa):

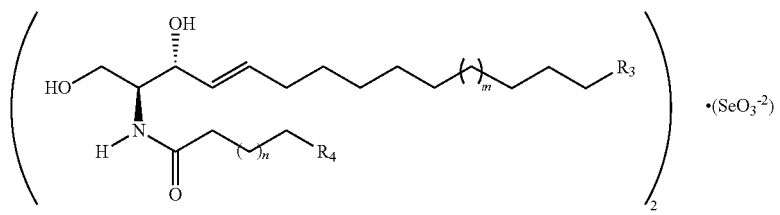

wherein: m is an integer between 1 and 5; n is an integer between 3 and 21; and $R_3$ and $R_4$ are each selected from —H and N-heterocycle, subject to the proviso that when $R_3$ is —H, $R_4$ is N-heterocycle and when Ra is N-heterocycle, $R_4$ is —H. In some embodiments, n is between 9 and 21. In some embodiments, m is 5, n is 13, $R_3$ is —H, and $R_4$ is pyridinium. Thus, in some embodiments, the ionic conjugate has the structure of LCL-767. See FIG. 1A. In some embodiments, m is 1, n is 15, $R_3$ is pyridinium, and $R_4$ is —H. Thus, in some embodiments, the ionic conjugate has the structure of LCL-768. See FIG. 1A.

In some embodiments, Y' is —CH(OH)— and $R_2$ is H; and the compound of Formula (III) is a compound of Formula (IIIb):

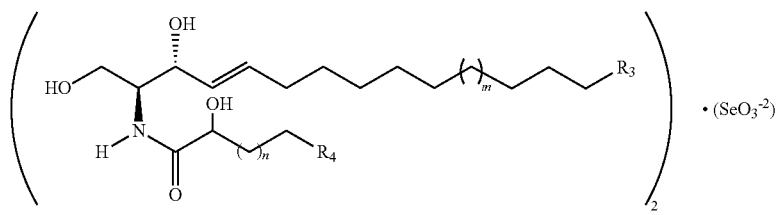

wherein: m is an integer between 1 and 5; n is an integer between 3 and 21; and $R_3$ and $R_4$ are each selected from —H and N-heterocycle, subject to the proviso that when $R_3$ is —H, $R_4$ is N-heterocycle and when Ra is N-heterocycle, $R_4$ is —H. In some embodiments, the acyl chain of the amide group of the compound of Formula (IIIb) can comprise between six and 18 carbons (including the carbonyl carbon). Thus, in some embodiments, n is between 3 and 15. In some embodiments, Ri is pyridinium and $R_4$ is H. In some embodiments, m is 5, n is 13, $R_3$ is pyridinium, and $R_4$ is H. See FIG. 1B.

In some embodiments, the presently disclosed subject matter provides pharmaceutical formulations comprising the ionic conjugates. Thus, in some embodiments, the composition can comprise an admixture of a pharmaceutically acceptable carrier and the ionic conjugate, and optionally one or more additional pharmaceutically acceptable additives known in the art for use in pharmaceutical formulations, such as pH adjusters, excipients, antimicrobial agents, flavoring additives, etc. Thus, in some embodiments, the presently disclosed subject matter provides a pharmaceutical formation comprising the ionic conjugate.

III. Uses of Sphingolipid-Based Selenium Compounds

According to the presently disclosed subject matter, disorders involving cell hyperproliferation can be treated and/or prevented by administration of a composition that comprises an ionic conjugate comprising a cationic ceramide and a selenite ion. Diseases and disorders involving cell overproliferation that can be treated and/or prevented include, but are not limited to cancers, pre-malignant conditions (e.g., hyperplasia, metaplasia, dysplasia), benign tumors, hyperproliferative disorders, and benign dysproliferative disorders. Cancer is characterized primarily by an increase in the number of abnormal cells derived from a given normal tissue, invasion of adjacent tissues by these abnormal cells, and lymphatic or blood-borne dissemination of the abnormal cells to distant sites in the subject. The presently disclosed subject matter encompasses methods for treating and/or preventing diseases and disorders wherein the treatment or prevention would be improved by administration of the compounds of the presently disclosed subject matter.

In some embodiments, "treatment" or "treating" refers to an amelioration of disease or disorder, or at least one discernible symptom thereof. "Treatment" or "treating" also refers to an amelioration of at least one measurable physical parameter associated with a disease or disorder that is not necessarily discernible by the subject. "Treatment" or "treating" can also refer to inhibiting the progression of a disease or disorder either physically (e.g., stabilization of a discernible symptom), physiologically (e.g., stabilization of a physical parameter), or both. "Treatment" or "treating" also refers to delaying the onset of a disease or disorder.

In some embodiments, the methods and compositions of the presently disclosed subject matter are useful as a preventative measure against disease or disorder. As used herein, "prevention" or "preventing" refers to a reduction of the risk of acquiring a given disease or disorder.

Accordingly, in some embodiments, the presently disclosed subject matter provides the use of the ionic conjugates (or formulations comprising the ionic conjugates) in treating disease, e.g., cancer or another hyperproliferative disorder. In some embodiments, the ionic conjugate or a formulation thereof can be provided for use in treating a head and neck cancer (e.g., HNSCC) or a brain cancer (e.g., GB).

In some embodiments, the presently disclosed subject matter provides a method of treating a disease, wherein the method comprises administering to a subject in need thereof a composition comprising an ionic conjugate as described herein or a ceramide prodrug or ceramide analog prodrug component thereof. In some embodiments, the disease is cancer or another hyperproliferative disorder. In some embodiments, the cancer is a head and neck cancer e.g., HNSCC. In some embodiments, the cancer is a brain cancer. In some embodiments, the brain cancer is a glioblastoma. In some embodiments, the glioblastoma is a temozolomide resistant glioblastoma.

In some embodiments, the administration of the ionic conjugate or a formulation thereof provides increased reduction in tumor cell load compared to treatment of the subject with a composition comprising a selenite compound (e.g., selenite anion) that is not provided as part of such a conjugate. In some embodiments, the administration of the ionic conjugate or formulation thereof provides reduced off-target selenite-related toxicity compared to treatment with a composition comprising a selenite compound (e.g., a selenite anion) that is not provided as part of an ionic conjugate as described herein. In some embodiments, the administration of the ionic conjugate provides increased reduction in tumor cell load and/or reduced off-target toxicity compared to treatment with a non-conjugated mixture of a selenium-containing compound and a sphingolipid-based therapeutic agent (e.g., wherein the selenium-containing compound and the sphingolipid-based therapeutic agent are administered at around the same time or at different times). In some embodiments, administration of the ionic conjugate provides effective treatment using a lower concentration of selenite anion than the concentration of selenite anion that would have been administered if the selenite anion was not part of an ionic conjugate with a sphingolipid-based compound (e.g., a cationic ceramide analog).

In some embodiments, administration of the ionic conjugate (or a formulation thereof) results in accumulation of the cationic ceramide in mitochondria of cancer cells and the induction of lethal mitophagy. This lethal mitophagy can be measured via cell death assays, by levels of aconitase 2

(ACO2, a mitochondrial matrix protein) or ATP (a cellular energy source produced in mitochondria) or can be visualized by confocal microscopy.

In some embodiments, the compositions of the presently disclosed subject matter are used to treat cancer or cancer metastasis. In some embodiments, the presently disclosed subject matter provides a method of treating cancer comprising administering to a subject in need of treatment thereof an effective amount of a compound of Formula (I), (II), (III), (IIIa), or (IIIb) or a pharmaceutical formulation thereof.

In some embodiments, the presently disclosed subject matter provides methods for treating or preventing diseases or disorders comprising administration of a compound of the presently disclosed subject matter in combination with other treatments.

Cancers and related disorders that can be treated and/or prevented by methods and compositions of the presently disclosed subject matter include, but are not limited to the following: leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, non-secretory myeloma, osteosclerotic myeloma, plasma cell leukemia, solitary plasmacytoma and extramedullary plasmacytoma; Waldenström's acroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, non-glial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytoma and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipidus; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; head and neck squamous cell cancers (HNSCCs), esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or ureter); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas. For a review of such disorders, see Fishman et al., *Medicine*, 2$^{nd}$ Ed., J. B. Lippinocott Co., Philadelphia, 1985; and Murthy et al., *Informed Decisions: The Complete Book of Cancer Diagnosis, Treatment, and Recovery*, Viking Penguin, Penguin Books, U.S.A., Inc., New York, 1997).

In some embodiments, the methods and compositions of the presently disclosed subject matter are used for the treatment and/or prevention of breast cancer, lung cancer, prostate cancer, melanoma, alveolar cancer, brain cancer, or head and neck cancer.

The compositions of the presently disclosed subject matter that inhibit ceramidase activity can also be administered to treat pre-malignant conditions and/or to prevent progression of a pre-malignant condition to a neoplastic or malignant state. Such prophylactic or therapeutic use is indicated in conditions known or suspected of preceding progression to neoplasia or cancer, in particular, where non-neoplastic cell growth comprising hyperplasia, metaplasia, or most particularly, dysplasia has occurred. For review of such abnormal growth conditions, see Robbins and Angell, *Basic Pathology*, 2$^{nd}$ Ed., W.B. Saunders Co., Philadelphia, 1976, pages 68-79).

Alternatively or in addition to the presence of abnormal cell growth characterized as hyperplasia, metaplasia, or dysplasia, the presence of one or more characteristics of a transformed phenotype or of a malignant phenotype displayed in vivo or displayed in vitro by a cell sample from a subject can indicate the desirability of prophylactic and/or therapeutic administration of a composition that inhibits ceramidase function. Characteristics of a transformed phenotype can include morphology changes, looser substratum attachment, loss of contact inhibition, loss of anchorage dependence, protease release, increased sugar transport, decreased serum requirement, expression of fetal antigens, etc.

In some embodiments, leukoplakia, a benign-appearing hyperplastic or dysplastic lesion of the epithelium, or Bowen's disease, a carcinoma in situ, are pre-neoplastic lesions indicative of the desirability of prophylactic intervention.

In some embodiments, fibrocystic disease (cystic hyperplasia, mammary dysplasia, particularly adenosis (benign epithelial hyperplasia) is indicative of the desirability of prophylactic intervention. The gene of the human acid ceramidase of the presently disclosed subject matter is localized on chromosome 8 (8p22). Based on this location, acid ceramidase can be involved in diseases associated with this region, in addition to the disease and disorder discussed above, which include adenocarcinoma (thyroid), acute myeloid leukemia, and squamous cell cancer, especially that which is associated with the nasopharynx region.

In other embodiments, a subject which exhibits one or more of the following predisposing factors for malignancy is treated by administration of an effective amount of a compound of the presently disclosed subject matter: a chromosomal translocation associated with a malignancy (e.g., the Philadelphia chromosome for chronic myelogenous leukemia, t(14; 18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, *Basic Pathology*, 2$^{nd}$ Ed., W.B. Saunders Co., Philadelphia, 1976, pages 112-113.

The presently disclosed subject matter also encompasses methods for treating and/or preventing a cancer or metastasis in a subject comprising in any order the steps of administering to the subject a compound of Formula (I), (II), (III), (IIIa), or (IIIb). In some embodiments, the compositions and methods of the presently disclosed subject matter can be used to prevent, inhibit, and/or reduce the growth and/or metastasis of cancerous cells. The administration of compound inhibits or reduces the growth and/or metastasis of cancerous cells by in some embodiments at least 99%, in some embodiments at least 95%, in some embodiments at least 90%, in some embodiments at least 85%, in some embodiments at least 80%, in some embodiments at least 75%, in some embodiments at least 70%, in some embodiments at least 65%, in some embodiments at least 60%, in some embodiments at least 55%, in some embodiments at least 50%, in some embodiments at least 45%, in some embodiments at least 40%, in some embodiments at least 35%, in some embodiments at least 30%, in some embodiments at least 25%, in some embodiments at least 20%, in some embodiments at least 15%, in some embodiments at least 10%, and in some embodiments at least 5% relative to the growth or metastasis in absence of the administration of said compound.

The presently disclosed subject matter also encompasses methods of disease treatment and/or prevention that provide better therapeutic profiles than current single agent therapies or even current combination therapies. Encompassed by the presently disclosed subject matter are combination therapies that have additive potency or an additive therapeutic effect while reducing or avoiding unwanted or adverse effects.

Other cancer treatment that can be used in combination of the administration of the compounds of the presently disclosed subject matter include the use of one or more compositions which include, but are not limited to, chemoagents, immunotherapeutics, cancer vaccines, anti-angiogenic agents, cytokines, hormone therapies, gene therapies, biological therapies, and radiotherapies. While maintaining and/or enhancing efficacy of treatment, the methods of the presently disclosed subject matter can also increase subject compliance, improve therapy, and/or reduce unwanted or adverse effects.

In some embodiments, a compound of the presently disclosed subject matter is administered to a subject receiving a treatment modality for the treatment of cancer wherein the subject might experience unwanted or adverse effects to treatment with the treatment modality alone (e.g., the treatment modality might be toxic or harmful at its effective dose, administered alone). Given the presently disclosed subject matter, the compound can improve the therapeutic benefit of the treatment modality such that the dosage and/or frequency of administration of the treatment modality can be lowered when administered in conjunction with the compound. In some embodiments, a compound of the presently disclosed subject matter is administered to allow lower and/or less frequent doses of chemotherapy and/or radiation therapy.

In some embodiments, the methods of the presently disclosed subject matter encompass the administration of one or more angiogenesis inhibitors such as, but not limited to angiostatin (plasminogen fragment); anti-angiogenic antithrombin Ill; anti-Flt-1 ribozyme sold under the trademark ANGIOZYME™; atrasentan (ABT-627); tanomastat (Bay 12-9566); Benefin; Bevacizumab; rebimastat (BMS-275291); cartilage-derived inhibitor (CDI); carboxyamidotriazole (CAI); CD59 complement fragment; CEP-7055; COL-3 (metastat); Combretastatin A-4; C-terminal fragment of type XVIII collagen (collage alpha-1(XVIII) chain) sold under the trademark ENDOSTATIN™; Fibronectin fragment; Gro-beta; Halofuginone; Heparinases; Heparin hexasaccharide fragment; humanized mouse monoclonal anti-vascular endothelial growth factor (VEGF) antibody (HMV833); Human chorionic gonadotropin (hCG); oglufanide disodium (IM-862); Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; matrix metalloproteinase inhibitor 270 (MMI 270; CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kDa fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiornolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates.

Additional examples of anti-cancer agents (e.g., chemotherapeutic) that can be used in conjunction with the presently disclosed subject matter, including pharmaceutical compositions and dosage forms and kits of the presently disclosed subject matter, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride: elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin (IL) II (including recombinant interleukin-2, or rIL-2), interferon alfa-2a; interferon α-2b; interferon α-n1; interferon α-n3; interferon β-I a; interferon γ-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; acute lymphoblastic leukemia tachykinin (ALL-TK) antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; Breakpoint Cluster Region-Abelson (BCR/ABL) antagonists; benzochlorins; benzoyistaurosporine; beta lactam derivatives; beta-alethine; betaclamycin B; betulinic acid; basic fibroblast growth factor (bFGF) inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide amino triazole; carboxyamidotriazole; CaRest M3; carnosine (CARN) 700; cartilage derived inhibitor; carzelesin; casein kinase inhibitors (ICOS); castanospermine; cecropin B; cetrorelix; chlorins; chloroquinoxaline sulfonamide; cicaprost; cis porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; fligrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin like growth factor 1 receptor inhibitor; interferon agonists; interferons; interleukins; iobenguane; iododoxorubicin; ipomeanol 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; macrophage migration inhibitory factor (MIF) inhibitor; mifepristone; miltefosine; mirimostim; mismatched double stranded RNA; mitoguazone; mitolactol; mitomycin analogues; mitonafide; mitotoxin fibroblast growth factor saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein tranaferase inhibitors; ras inhibitors; ras GTPase-activating protein (GAP) inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; sarmustine (SarCNU); sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; ubiquitin-conjugating enzyme (UBC) inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Representative additional anti-cancer drugs are 5-fluorouracil and leucovorin.

These two agents are particularly useful when used in methods employing thalidomide and a topoisomerase inhibitor.

In some embodiments, the treatment of the presently disclosed subject matter further includes the administration of one or more immunotherapeutic agents, such as antibodies and immunomodulators, which include, but are not limited to, trastuzumab sold under the trademark HERCEPTIN®, rituximab sold under the trademark RITUXAN®, oregovomab sold under the trademark OVAREX™, edrecolomab sold under the trademark PANOREX®, Mitumomab (BEC2), Cetuximab IMC-C225, MEDI-523 sold under the trademark VITAXIN™, alemtuzumab sold under the trademark CAMPATH® I/H, Smart M195, epratuzumab sold under the trademark LYMPHOCIDE™, Smart I D10, and HLA-DRB1 sold under the trademark ONCOLYM™, rituximab, gemtuzumab, or trastuzumab.

In some embodiments, the treatment of the presently disclosed subject matter further includes administering one or more anti-angiogenic agents, which include, but are not limited to, angiostatin, thalidomide, kringle 5, endostatin, other Serpins, anti-thrombin, 29 kDa N-terminal and 40 kDa C-terminal proteolytic fragments of fibronectin, 16 kDa proteolytic fragment of prolactin, 7.8 kDa proteolytic fragment of platelet factor-4, a 13-amino acid peptide corresponding to a fragment of platelet factor-4 (see Maione et al., Cancer Res., 51, 2077-2083, (1991)), a 14-amino acid peptide corresponding to a fragment of collagen I (see Tolsma et al., *J. Cell Biol.*, 122, 497-511 (1993)), a 19 amino acid peptide corresponding to a fragment of Thrombospondin I (see Tolsma et al., *J. Cell Biol.*, 122, 497-511 (1993)), a 20-amino acid peptide corresponding to a fragment of SPARC (see Sage et al., *J. Cell Biochem.*, 57, 127-140 (1995)), or any fragments, family members, or derivatives thereof, including pharmaceutically acceptable salts thereof.

In some embodiments, the treatment method further comprises the use of radiation.

In some embodiments, the treatment method further comprises the administration of one or more cytokines, which include, but are not limited to, lymphokines, tumor necrosis factors, tumor necrosis factor-like cytokines, lymphotoxin-α, lymphotoxin-β, interferon-α, interferon-β, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40 (CD134), CD27, CD30, CD40, or CD137 ligands, Fas/Fas ligand, tumor necrosis factor ligand superfamily member 9 (4-1BBL), endothelial monocyte activating protein or any fragments, family members, or derivatives thereof, including pharmaceutically acceptable salts thereof.

In some embodiments, the treatment method further comprises hormonal treatment. Hormonal therapeutic treatments comprise hormonal agonists, hormonal antagonists (e.g., flutamide, tamoxifen, leuprolide acetate (sold under the trademark LUPRON™), LH-RH antagonists), inhibitors of hormone biosynthesis and processing, steroids (e.g., dexamethasone, retinoids, betamethasone, cortisol, cortisone, prednisone, dehydrotestosterone, glucocorticoids, mineralocorticoids, estrogen, testosterone, progestins), antigestagens (e.g., mifepristone, onapristone), and anti-androgens (e.g., cyproterone acetate).

General techniques that can be employed for the determination of effective doses and administration of such compounds are known to the skilled artisan. Any technique which serves to selectively administer chemicals to a cell population of interest can be used, for example, by using a delivery complex. Such a delivery complex can comprise an appropriate chemical and a targeting agent. Such targeting agents can comprise, for example, sterols, lipids, viruses or target cell specific binding agents.

IV. Pharmaceutical Preparation and Methods of Administration

The compounds described herein can be administered to a subject at therapeutically effective doses to treat or prevent diseases and disorder discussed above. A therapeutically effective dose refers to that amount of a compound sufficient to result in a healthful benefit in the treated subject. See the *Physicians' Desk Reference®* (53$^{rd}$ ed., 1999).

The term "subject" as used herein refers to a member of any invertebrate or vertebrate species. The methods of the presently disclosed subject matter are particularly useful for warm-blooded vertebrates. Thus, the presently disclosed subject matter concerns mammals and birds. More particularly provided is the treatment of mammals such as humans, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the use of the disclosed methods and compositions on birds, including those kinds of birds that are endangered, kept in zoos or as pets, as well as fowl, and more particularly domesticated fowl, e.g., poultry, such as turkeys, chickens, ducks, geese, guinea fowl, and the like, as they are also of economic importance to humans.

Thus, the subject to which a compound of the presently disclosed subject matter is administered is in some embodiments an animal, including but not limited to mammal such as non-primate (e.g., cows, pigs, horses, chickens, cats, dogs, rats, etc.), or a primate (e.g., a monkey such as acynomolgous monkey or a human). In some embodiments, the subject is a human. The composition of the presently disclosed subject matter can be utilized for the prevention of a variety of cancers, e.g., in individuals who are predisposed as a result of familial history or in individuals with an enhanced risk to cancer due to environmental factors.

The methods and compositions of the presently disclosed subject matter can be used in subjects who are treatment naïve and/or in subjects who have previously received and/or are currently receiving treatment with other pharmaceutical agents or combinations, including but not limited to anti-cancer agents. Other subjects can include subjects that have metastasis or no metastasis.

The methods and compositions of the presently disclosed subject matter are useful not only in untreated subjects but are also useful in the treatment of subjects partially or completely un-responsive to other treatments. In some embodiments, the presently disclosed subject matter provides methods and compositions useful for the treatment of diseases or disorders in subjects that have been shown to be or might be refractory or non-responsive to therapies comprising the administration of other agents.

IV.A. Effective Dose

Toxicity and therapeutic efficacy of compositions can be determined by standard pharmaceutical procedures in cell cultures or experimental animals (e.g., for determining the $LD_{50}$ (the dose lethal to 50% of the population) and the $ED_{50}$ (the dose therapeutically effective in 50% of the population)). The dose ratio between toxic and therapeutic effects is the therapeutic index and it can be expressed as the ratio $LD_{50}/ED_{50}$, In some embodiments, compounds that exhibit large therapeutic indices are employed. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies in some embodiments within a range of circulating concentrations that include the $ED_{60}$ with little or no toxicity. For example, the dosage can range from in some embodiments 10 nM to 100 µM and in some embodiments 1 to 10 µM or greater. The dosage can vary within this range depending upon the dosage form employed and the route of administration utilized. For any composition used in the methods of the presently disclosed subject matter, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

Suitable daily doses for the treatment or prevention of a disorder described herein can be readily determined by those skilled in the art. A recommended dose of a composition of the presently disclosed subject matter is from about 0.1 mg to about 100 mg per day, given as a single once-a-day dose in the morning or as divided doses throughout the day. In some embodiments, a daily dose is from about 2 mg to about 25 mg per day and in some embodiments a daily dose is from about 5 mg to about 10 mg per day.

The anti-cancer activity of the methods and compositions used in accordance with the presently disclosed subject matter also can be determined by using various experimental animal models of such as cancer animal models such as SCID mouse model or nude mice with human tumor grafts known in the art and described in Yamanaka et al. (*Microbiol. Immunol.*, 45, 507-514 (2001)).

In some embodiments, the methods and compositions of the presently disclosed subject matter are tested in vitro, and then in vivo, for the desired therapeutic or prophylactic activity, prior to use in a subject (e.g., a human), For example, in vitro assays which can be used to determine whether administration of a specific therapeutic protocol is indicated, include in vitro cell culture assays in which a subject tissue sample is grown in culture, and exposed to or otherwise administered a protocol, and the effect of such protocol upon the tissue sample is observed. A lower level of proliferation or survival of the contacted cells indicates that the composition is effective to treat the condition in the subject. Alternatively, instead of culturing cells from a subject, compositions can be screened using cells of a tumor or malignant cell line. Many assays standard in the art can be used to assess such survival and/or growth; for example, cell proliferation can be assayed by measuring $^{3}$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc. As described above, lethal mitophagy can be measured via cell death assays, by levels of aconitase 2 (ACO2, a mitochondrial matrix protein) or ATP (a cellular energy source produced in mitochondria) or can be visualized by confocal microscopy.

Prior to testing in humans, compositions for use in the presently disclosed methods can be tested in suitable animal model systems, including but not limited to in rats, mice, chicken, cows, monkeys, rabbits, etc. The principle animal models for cancer known in the art and widely used include mice, as described in Hann et al. (*Curr. Opin. Cell Biol.*, 13, 778-784 (2001)), which is incorporated herein by reference in its entirety.

Further, any assays known to those skilled in the art can be used to evaluate the prophylactic and/or therapeutic utility of the methods and compositions disclosed herein for treatment, prophylaxis, management, and/or amelioration of one or more symptoms associated with a disease or disorder as described herein.

IV.B. Formulations and Use

Various methods can be used to administer a compound of the presently disclosed subject matter. Methods of introduction include but are not limited to intradermal, intramuscular, intraperitoneal, intravenous, subcutaneous, intranasal, epidural, inhalation, insufflation (either through the mouth or the nose), oral, buccal, or rectal routes. The compositions can be administered by any convenient route, for example by infusion or bolus injection, by absorption through epithelial or mucocutaneous linings (e.g., oral mucosa, rectal and intestinal mucosa, etc.) and can be administered together with other biologically active agents. Administration can be systemic or local. In addition, it can be desirable to introduce the pharmaceutical compositions of the presently disclosed subject matter into the central nervous system by any suitable route, including intraventricular and intrathecal injection; intraventricular injection can be facilitated by an intraventricular catheter, for example, attached to a reservoir, such as an Ommaya reservoir. Pulmonary administration can also be employed, e.g., by use of an inhaler or nebulizer and formulation with an aerosolizing agent.

In some embodiments, it is desirable to administer the compositions of the presently disclosed subject matter locally to the area in need of treatment. This can be achieved, for example, and not by way of limitation, by local infusion during surgery, by a catheter, by a suppository, or by an implant. The implant can be a porous, non-porous, or gelatinous material, including membranes, such as sialastic membranes, or fibers, by way of example and not limitation.

In some embodiments, the presently disclosed compounds can be delivered in a vesicle, in particular a liposome. See Langer, *Science*, 249, 1527-1533 (1990); and Treat et al., in *Liposomes in the Therapy of Infectious Disease and Cancer*, Lopez-Berestein and Fidler (eds.), Liss, New York, 1989, pp. 317-327 and 353-365.

In some embodiments, the presently disclosed compounds can be delivered in a controlled release system. In some embodiments, a pump is used. See Langer, *Science*, 249, 1527-1533 (1990); Sefton, *CRC Crit. Ref., Biomed. Eng.*, 14, 201 (1987); Buchwald et al., *Surgery*, 88, 507 (1980); and Saudek, et al., *N. Engl. J. Med.*, 321, 574 (1989). In some embodiments, polymeric materials can be used. See Langer and Wise (eds.), Medical Applications of Controlled Release, CRC Press, Boca Raton, Florida, 1974; Smolen and Ball (eds.), Controlled Drug Bioavailability, Drug Product Design and Performance, Wiley, New York, 1984; Ranger and Peppas, J. Macromol. Sci. Rev. Macromol. Chem., 23, 61 (1983); see also Levy et al., *Science*, 228, 190 (1985); During et. al., *Ann. Neurol.*, 25, 351 (1989); and Howard et al., *J. Neurosurg.*, 71, 105 (1989). In some embodiments, a controlled release system can be placed in proximity of the therapeutic target, thus requiring only a fraction of the systemic dose. See Goodson, in *Medical Applications of Controlled Release*, Langer and Wise (eds.), CRC Press, Boca Raton, Florida, 1974. Other controlled release systems are discussed in Langer (*Science*, 249, 1527-1533 (1990)).

Other methods of delivery of the therapeutics of the presently disclosed subject matter can be used for example, as described in U.S. Pat. No. 5,679,350, which is incorporated by reference in its entirety.

As described hereinabove, the presently disclosed subject matter also provides pharmaceutical compositions. Such compositions comprise a therapeutically effective amount of one or more compounds of Formula (I), (II), (III), (IIIa), or (IIIb) of the presently disclosed subject matter and a pharmaceutically acceptable carrier. "Pharmaceutically acceptable" refers to those carriers, compositions, and/or dosage forms that are, within the scope of sound medical judgment, suitable for contact with the tissues of human beings and/or other animals without excessive toxicity, irritation, allergic response, or other problems or complications commensurate with a reasonable benefit/risk ratio. Thus, in some embodiments, the presently disclosed compounds can be provided in formulations comprising the compound and a carrier that is pharmaceutically acceptable for use in humans. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remingtons Pharmaceutical Sciences* (1990). Such compositions will contain in some embodiments a therapeutically effective amount of the ionic conjugate together with a suitable amount of carrier so as to provide the form for proper administration to the subject. The formulation should suit the mode of administration.

In some embodiments, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lidocaine to ease pain at the site of the injection, Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The amounts of the compounds of the presently disclosed subject matter which are effective in the treatment of a particular disorder or condition can depend on the nature of the disorder or condition and can be determined by standard clinical techniques. In addition, in vitro assays and animal models can optionally be employed to help identify optimal dosage ranges. The precise dose to be employed in the formulation can also depend on the route of administration and the seriousness of the disease or disorder, and should be determined according to the judgment of the practitioner and each subject's circumstances.

In some embodiments, the compounds of the presently disclosed subject matter are administered intramuscularly. Suitable dosage ranges for the intramuscular administration are generally in some embodiments about 10 µg to 1 mg per dose and in some embodiments about 10 µg to 100 µg per dose. In some embodiments, the composition is administered in two doses, where the second dose is administered 24 hours after the first dose. In some embodiments, a composition of the presently disclosed subject matter is administered in three doses, with one dose being administered on each of days 1, 4, and 7 of a 7-day regimen.

Suppositories generally contain active ingredient in the range of 0.5% to 10% by weight; oral formulations generally contain 10% to 95% active ingredient.

The presently disclosed subject matter also provides a pack or kit for therapeutic use comprising one or more containers filled with one or more of the ingredients of the pharmaceutical compositions of the presently disclosed subject matter. Optionally associated with such container(s) can be a notice in the form prescribed by a governmental agency regulating the manufacture, use, or sale of pharmaceuticals and/or diagnostic products, which notice reflects approval by the agency of manufacture, use, or sale for human administration.

Pharmaceutical compositions for use in accordance with the presently disclosed subject matter can be formulated in conventional manner using one or more physiologically acceptable carriers or excipients.

For oral administration, the pharmaceutical compositions can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional approaches with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring, and sweetening agents as appropriate.

Preparations for oral administration can be suitably formulated to give controlled release of the active agent in the composition.

For buccal administration, the compositions can take the form of tablets or lozenges formulated in conventional manner.

For administration by inhalation, the compositions for use according to the presently disclosed subject matter can be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide, or other suitable gas). In the case of a pressurized aerosol, the dosage unit can be determined by providing a valve to deliver a metered amount. Capsules and cartridges of e.g., gelatin, for use in an inhaler or insufflator can be formulated containing a powder mix of the composition and a suitable powder base such as lactose or starch.

The compositions can be formulated for parenteral administration (i.e., intravenous or intramuscular) by injection via, for example, bolus injection or continuous infusion. Formulations for injection can be presented in unit dosage form, e.g., in ampoules or in multi-dose containers, with an added preservative. The compositions can take such forms as suspensions, solutions, or emulsions in oily or aqueous vehicles, and can contain formulatory agents such as suspending, stabilizing, and/or dispersing agents. Alternatively, the active ingredient can be in powder form for constitution with a suitable vehicle, e.g., sterile pyrogen-free water, before use.

The compositions can also be formulated in rectal compositions such as suppositories or retention enemas, e.g., containing conventional suppository bases such as cocoa butter or other glycerides.

In addition to the formulations described previously, the compositions can also be formulated as a depot preparation. Such long acting formulations can be administered by implantation (for example subcutaneously or intramuscularly) or by intramuscular injection. Thus, for example, the compositions can be formulated with suitable polymeric or hydrophobic materials (for example, as an emulsion in an acceptable oil) or ion exchange resins, or as sparingly soluble derivatives, for example, as a sparingly soluble salt.

EXAMPLES

The following Examples provide illustrative embodiments. In light of the present disclosure and the general level of skill in the art, those of skill can appreciate that the following Examples are intended to be exemplary only and that numerous changes, modifications, and alterations can be employed without departing from the scope of the presently disclosed subject matter.

General Methods and Materials

Immunofluorescence:
UM-SCC-22A (squamous carcinoma) cells (50,000 per well) were plated on glass coverslips in a six-well plate for 18 hours. Cells were fixed and permeabilized using 4% paraformaldehyde (20 min) and 0.1% Triton X-100 in 1× phosphate-buffered saline (PBS) (pH 7.4) for 10 min. The cells were then blocked with 1% bovine serum albumin (BSA)/PBS (pH 7.4) for 1 hour. Cells were incubated for 18 hours at 4° C. with antibodies (e.g., antibodies specific for ceramide, LC3, Tom20, green fluorescent protein (GFP), CerS1, or GM130) (1:50) in blocking solution, followed by Alexa Fluor 488- or Alexa Fluor 594-conjugated secondary antibodies (Thermo Fisher Scientific, Waltham, Massachusetts, United States of America; 1:1000) for 1 hour. Immunofluorescence was performed using a Leica TCS SP2 AOBS confocal microscope (Leica Microsystems, Wetzler, Germany), an Olympus FV10i microscope (Olympus Corporation, Tokyo, Japan) with 543- and 488-nm channels for visualizing green and red fluorescence, or a Zeiss LSM 880 NLO Quasar confocal/multiphoton microscope with a Fast Airyscan super-resolution detector (Carl Zeiss, AG, Oberkochen, Germany). Images were taken at 63× magnification. At least three random fields were selected for image quantification.

Immunoprecipitation and Western Blotting:

Cellular lysates in radioimmunoprecipitation assay (RIPA) buffer containing a protease inhibitor cocktail (Sigma-Aldrich, St. Louis, Missouri, United States of America) were normalized by the total protein level and analyzed by sodium dodecyl sulfate-polyacrylamide gel electrophoresis (SDS-PAGE) and immunoblotting with corresponding antibodies. For immunoprecipitation, precleared cytosolic fractions were incubated overnight with 2 µg of corresponding antibodies at 4° C., followed by 1-hour incubation with Protein A/G Agarose (Santa Cruz Biotechnology, Inc., Dallas, Texas, United States of America) (50 µl of a 50% slurry). Resin was washed three to five times, and pulled-down proteins were analyzed by SDS-PAGE and Western blotting with corresponding antibodies.

The antibodies used for Western blotting were as follows: translocase of outer mitochondrial membrane 20 (TOM20) (cat #sc-17764, RRID:AB_628381; Santa Cruz Biotechnology, Inc., Dallas, Texas, United States of America), LC3B (cat #2775, RRID:AB_915950; Cell Signaling Technology, Inc., Danvers, Massachusetts, United States of America), ACO2 (cat #6922S, RRID:AB_10828218: Cell Signaling Technology, Inc., Danvers, Massachusetts, United States of America), GFP (cat #14-6774-63, RRID:AB_468332; Thermo Fisher Scientific), cystein S-nitrosylated (SNO-Cys) (cat #09002-75; U.S. Biological Life Sciences, Salem, Massachusetts, United States of America), dynamin-like protein 1 (DLP1) (cat #611112; BD Biosciences, San Jose, California, United States of America), actin (cat #A2066, RRID:AB_476693: Sigma-Aldrich, St. Louis, Missouri, United States of America), ceramide (MD15B4; Enzo Life Sciences, Inc., Farmingdale, New York, United States of America), cis-Golgi matrix protein 130 kDa (GM130) (cat #sc-30100, RRID:AB_2232778; Santa Cruz Biotechnology, Inc., Dallas, Texas, United States of America).

Cell Viability Assay:

Cell viability was assessed by 3-(4,5-dimethylthiazol-2-yl)-2,5-diphenyltetrazolium bromide (MTT) cell proliferation assay using cell Titer 96 kit (Promega Corporation, Madison, Wisconsin), or by measuring ATP using a luminescent cell viability assay sold under the trademark CELL-TITER-GLO™ Luminescent Cell Viability Assay (Promega Corporation, Madison, Wisconsin) according to the manufacturer's directions.

Detection of LC3 Activation:

LC3 activation was assessed with the autophagy detection kit sold under the trademark CYTO-ID™ (Enzo Life Sciences Inc., Farmingdale, New York, United States of America) in live cells using fluorescence microscopy, according to the manufacturer's instructions.

Example 1

Compound Synthesis

LCL-767 (D-erythro-16-(1'-pyridinium)-N-hexadecanoyl-sphingosine selenite)

This compound was prepared by ion exchange method using as a starting material D-erythro-16-(1'-pyridinium)-N-hexadecanoyl-sphingosine bromide (LCL-30)[1], sodium selenite, and an ion exchange resin (sold under the trademark AMBERLYST™ A-26, DDP Specialty Electronic Materials, Wilmington, Delaware, United States of America), according to a previously described procedure.[2]

The pure LCL-767 was obtained by recrystallization from acetone-ethyl acetate-ethanol (4:1:0.5, v/v) as a pale yellow microcrystalline solid. Yield 78%. Reversed phase thin-layer chromatography (RP TLC) (C18 Silica, $CH_3CN/CH_3OH$/1M $NH_4Cl$ (aq), 4:1:0.5, v/v); Rr 0.20; Reversed-phase high-performance liquid chromatography (RP HPLC) (Column: sold under the trademark X-Bridge BEH C8, 2.5 mm (Waters Corporation, Milford, Massachusetts, United States of America); Mobile phase: (A) Mixture of 2 mM $NH_4COOH$ and 0.2% HCOOH in water: (B) 1 mM NH4COOH and 0.2% HCOOH in methanol; Flow: 0.5 ml/mm. Gradient from 18% A to 82% B) RT: 6.58 min. $^1H$ NMR (600 MHz, $(CD_3OD)$ δ 8.60 (m, 3H, 2,4 and 6-HPy), 8.10 (t, 2H, J=7.0, 3,5-HPy), 5.66 (dtd, 1H, J=15.2, 6.7, 0.8, 5-H), 5.42 (ddt, 1H, J=15.3, 7.5, 1,3, 4-H), 4.62 (t, 2H, J=7.5, C(16)H2-pyridinium ring), 4.06 (t, 1H, J=7.4, 3-H), 3.82 (dt, 1H, J=7.5, 5.0, 2-H), 3.67 (d, 2H, J=5.1, 1-Ha,b), 2.16 (t, 2H, J=7.5, $COCH_2$), 2.06 (m, 4H, C(15)H2C(16)H$_2$-pyridinium ring and C(6)H2), 1.56 (m, 2H, $COCH_2CH_2$), 1.38 (m, 4H, C(14)H$_2$C(15)H2C(16)H2-pyridinium ring and C(7)H$_2$), 1.28 (m, 40H, CH$_2$), 0.88 (t, 3H, J=7.0, CH$_3$; electrospray ionization mass spectrometry (ESI-MS) ($CH_3OH$, relative intensity, %) m/z 615.0 (M+, 100). Calcd. for $[C_{39}H_{71}N_2O_3]^+$ m/z 615.5.

LCL-768 (D-erythro-14-(1'-pyridinium)-N-octadecanoyl-sphingosine selenite)

This compound was prepared by ion exchange method using as a starting material D-erythro-14-(1'-pyridinium)-N-octadecanoyl-sphingosine bromide (LCL-461; see its procedure below), sodium selenite, and an ion exchange resin (sold under the trademark AMBERLYST™ A-26, DDP Specialty Electronic Materials, Wilmington, Delaware, United States of America), according to a previously described procedure.[2]

The pure LCL-768 was obtained by recrystallization from acetone-ethyl acetate-ethanol (4:1:0.5, v/v) as a bright orange microcrystalline solid. Yield 74%. RP TLC $R_f$: 0.22 (C18 Silica, $CH_3CN/CH_3OH$/1M $NH_4Cl$ (aq), 4:1:0.5, v/v); RP HPLC (Column: sold under the trademark X-Bridge BEH C8, 2.5 µm (Waters Corporation, Milford, Massachusetts, United States of America) Mobile phase: (A) Mixture of 2 mM $NH_4COOH$ and 0.2% HCOOH in water: (B) 1 mM $NH_4COOH$ and 0.2% HCOOH in methanol; Flow: 0.5 ml/min., Gradient from 18% A to 82% B) RT: 6.03 min. $^1H$ NMR (600 MHz, $(CD_3OD)$ δ 9.03 (dd, 2H, J=5.8, 1.2, 2,6-H$_{Py}$) 8.61 (tt, 1H, J=7.8, 1.2 4-H$_{Py}$), 8.13 (t, 2H, J=7.0, 3,5-H$_{Py}$), 5.67 (dtd, 1H, J=15.3, 6.7, 0.8, 5-H), 5.46 (ddt, 1H, J=15.3, 7.5, 1.3, 4-H), 4.64 (t, 2H, J=7.5, C(14)H$_2$-pyridinium ring), 4.05 (t, 1H, J=7.4, 3-H), 3.86 (dt, 1H, J=7.5, 5.0, 2-H), 3.67 (d, 2H, J=5.1, 1-Ha,b), 2.18 (t, 2H, J=7.5, COCH$_2$), 2.02 (m, 4H, C(13)H$_2$C(14)H$_2$-pyridinium ring and C(6)H$_2$), 1.57 (m, 2H, COCH$_2$CH$_2$), 1.38 (m, 4H, C(12)H$_2$C(13)H$_2$C(14)H$_2$-pyridinium ring and C(7)H$_2$), 1.27 (m, 40H, CH$_2$), 0.88 (t, 3H, J=7.0, CH$_3$). ESI-MS (CH$_3$OH, relative intensity, %) m/z 587.0 (M$^+$, 100). Calcd. for [C$_{37}$H$_{67}$N$_2$O$_3$]$^+$ m/z 587.5.

LCL-461 (D-erythro-2-N-octadecanoyl-14-(1'-pyridinium)-sphingosine bromide). This compound was prepared by cross metathesis of D-erythro-C18-ceramide with 11-bromo-undecene following cationization of the formed ω-bromo-C18-ceramide with pyridine according to the methods described previously.[13] (A). Cross-metathesis of D-erythro-C18-Ceramide with 11-bromo-1-undecene. To a well-stirred mixture of D-erythro-C18-Ceramide (400 mg, 0.71 mmol) and the Grubbs' catalyst (2$^{nd}$ generation: benzylidene[1,3-bis-(2,4,6-trimethylphenyl)-2-imidazolidinylidene]dichloro(tricyclohexylphosphine) ruthenium; 95 mg, 15% mol) in anhydrous dichloromethane (20 mL) 11-bromo-1-undecene (1.7 mL, 7.4 mmol, 95%) was added drop-wise at room temperature with the exclusion of moisture, After the addition was completed, the reaction mixture was stirred and heated under reflux for 1.5 h. The reaction mixture was evaporated under reduced pressure to dryness and the obtained residue was washed with n-hexane (2×5 mL). The afforded crude product was purified by silica gel flash column chromatography (CHCl$_3$-methanol (15:1, v/v). The fractions within the R$_f$ values of 0.48-0.51 (CHCl$_3$-MeOH, 8:1, v/v/) were collected and evaporated to dryness to give the intermediate product, D-erythro-2-N-octadecanoyl-14-bromo-sphingosine (209 mg, 50% yield; pale brown microcrystalline solid after recrystallization from acetone-ethyl acetate, 1:3, v/v; TLO (silica gel, EtOAc-EtOH-CH$_3$CN, 20:1:1, v/v) R$_f$ 0.36. This material was taken directly to the next step for cationization with pyridine.

(B). Cationization of D-eryhtro-14-bromo-C18-Ceramide. A mixture of D-erythro-2-N-octadecanoyl-14-bromo-sphingosine (150 mg, 0.25 mmol), anhydrous pyridine (2 mL) and anhydrous toluene (3 mL) was heated in a closed glass test-tube in an oil bath at 85-95° C. over 7 hours. The reaction mixture was cooled down to room temperature and evaporated under reduced pressure to dryness following drying of the residue in a high vacuum for 2 hrs. The obtained residue was washed with n-hexane (2×3 mL) following ethyl-acetate-n-hexane (5×2 mL, 4:1, v/v). The crude product was recrystallized from acetone-ethyl acetate (1:2; v/v) to give LCL-461 (110 mg, 65% yield) as a grey microcrystalline powder. Analytical sample of LCL-461 was obtained by recrystallization from anhydrous acetone-ethyl acetate (3:1, v/v) as a white microcrystalline solid. TLC R$_f$=0.22 (C18RP-SiO$_2$; CH$_3$CN/CH$_3$OH/1M NH$_4$Cl, 4:1:0.5, v/v). RIP HPLC (Column: sold under the trademark X-Bridge BEH C8, 2.5 μm (Waters Corporation, Milford, Massachusetts, United States of America); Mobile phase: (A) Mixture of 2 mM NH$_4$COOH and 0.2% HCOOH in water: (B) 1 mM NH$_4$COOH and 0.2% HCOOH in methanol; Flow: 0.5 ml/min., Gradient from 18% A to 82% B) RT: 6.03 min. $^1$H NMR (500 MHz, CDCl$_3$) δ 9.37 (d, 2H, J=6.0, 2,6-H-Py) 8.47 (t, 1H, J=7.8, 4-H-Py), 8.11 (t, 2H, J=7.1, 3,5-H-Py), 6.80 (d, 1H, J=6.7, NH), 5.73 (dtd, 1H, J=15.2, 6.6, 0.6, 5-H), 5.52 (ddt, 1H, J=15.2, 6.5, 1.2, 4-H), 4.96 (t, 2H, J=7.5, C(14)H$_2$-pyridinium ring), 4.30 (m, 1H, 3-H), 3.93 (dd, 1H, J=11.1, 4.5, 1-Ha), 3.91 (m, 2H, 2-H) 3.69 (dd, 1H, J=11.1, 2.7, 1-Hb), 2.29 (t, 2H, J=7.4, COCH2), 2.06 (m, 4H, C(13)H$_2$C(14)H$_2$-pyridinium ring and C(6)H$_2$) 1.65 (m, 2H, COCH$_2$CH$_2$), 1.26 (m, 40H, CH$_2$), 0.88 (t, 3H, J=7.1, CH$_3$). ESI-MS (CH$_3$OH, relative intensity, %) m/z 587.40 (M$^+$, 100%). Calcd. for [C$_{37}$H$_{67}$N$_2$O$_3$]$^+$ m/z 587.51. ESI-MS/MS (daughter ions recorded at 40 eV) m/z 587.57 (Mt, 82%), 224.17 ([M-C$_{16}$H$_{36}$O$_2$—C$_5$H$_5$N]$^+$ 32%), 206.17 ([M-C$_{18}$H$_{36}$O$_2$—C$_5$H$_5$N—H$_2$O]$^+$, 100%), 194.17 (12%), 30.16 ([C$_5$H$_6$N]$^+$, 10%).

Example 2

Anticancer Effects of SPL-BSes

Figure 2A:
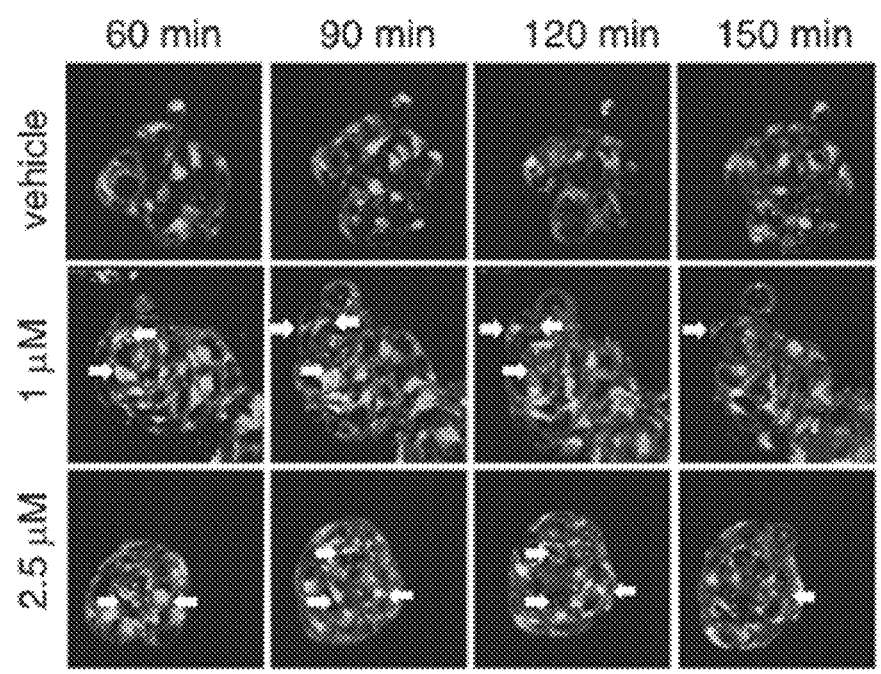
FIG. 2A is a series of confocal microphotographs of live head and neck squamous cell carcinoma (HNSCC-1A) cells treated with 2.5 micromolar (2.5 µM), 1.0 µM, or 0 µM (vehicle) concentrations of LCL-768, one of the compounds shown in FIG. 1A. The cells were stained for mitochondria and lysosomes and the microphotographs were taken at the indicated times (60 minutes (min), 90 min, 120 min, or 150 min) after addition of LCL-768. Arrows indicate regions of mitophagy.
Figure 2B:
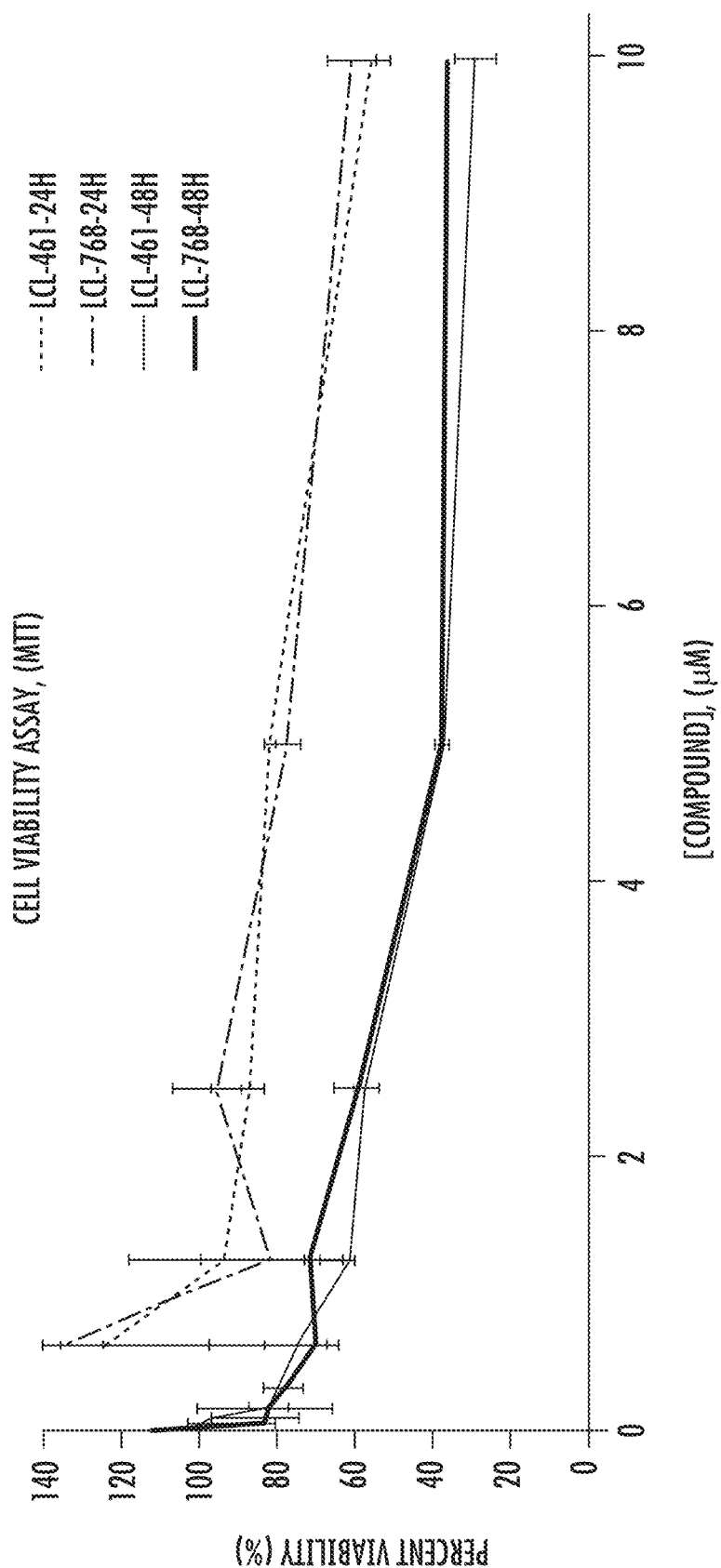
FIG. 2B is a graph showing the cell viability (measured as percent (%) viability) determined via 3-(4,5-dimethylthiazol-2-yl)-2,5-dimethyltetrazolium bromide (MIT) assay for head and neck squamous cell carcinoma (HNSCC-1A) cells treated for 24 or 48 hours with LCL-768, one of the presently disclosed sphingolipid-based selenium (SPL-BSe) compounds, as compared to cells treated for 24 or 48 hours with a sphingolipid-based compound (LCL-461) that is not conjugated to selenite anion.

Live-cell confocal microscopy of HNSCC-1A cells show mitophagy occurring within 90 minutes of exposure to low concentrations (1 and 2.5 μM) of LCL-768. See FIG. 2A. Cell death assays show similar IC$_{50}$ values for compounds LCL461 and LCL-768: about 10 μM and 4 μM at 24 and 48 hours, respectively See FIG. 28. The structure of LCL-461 is similar to that of the ceramide analog components of LCL-768. See Scheme 1, below and FIG. 1A.

Scheme 1. Structure of LCL461.

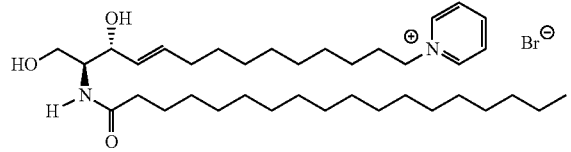

Figure 3A:
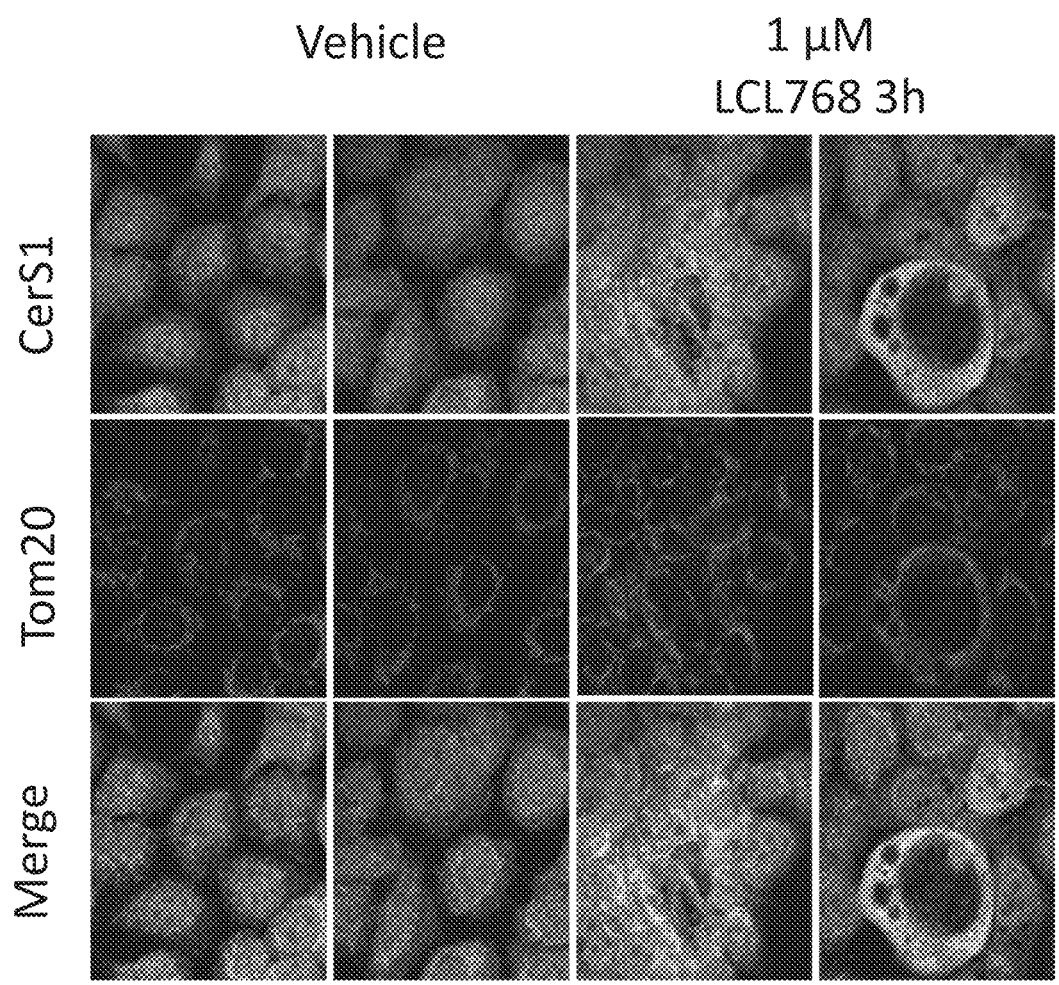
FIG. 3A is a series of confocal microscopy images of cells treated with 1 micromolar (1 µM) concentrations of a pyridinium-substituted ceramide-based selenium conjugated compound (LCL-768) or vehicle for 3 hours and labeled for Ceramide Synthase 1 (CerS1; top row), mitochondria (middle row) or both (bottom row).
Figure 3B:
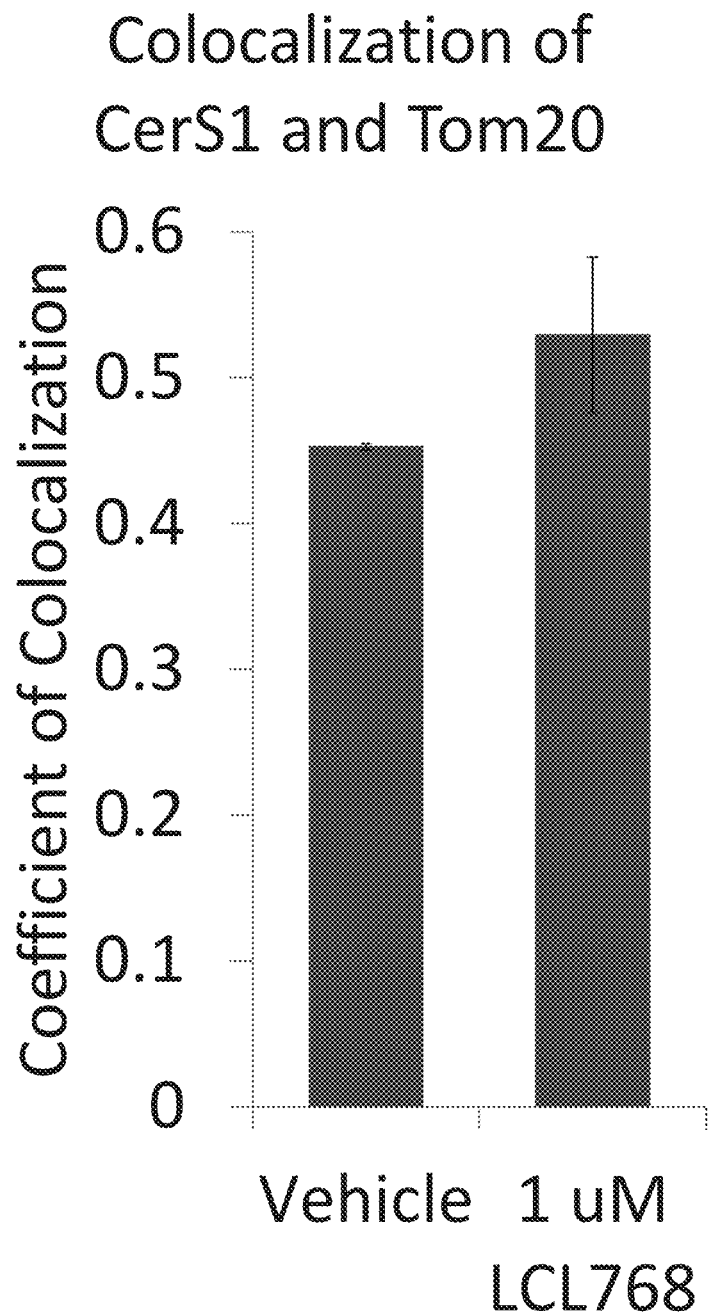
FIG. 3B is a graph showing the coefficient of colocalization based on selected images shown in FIG. 3A.
Figure 4:
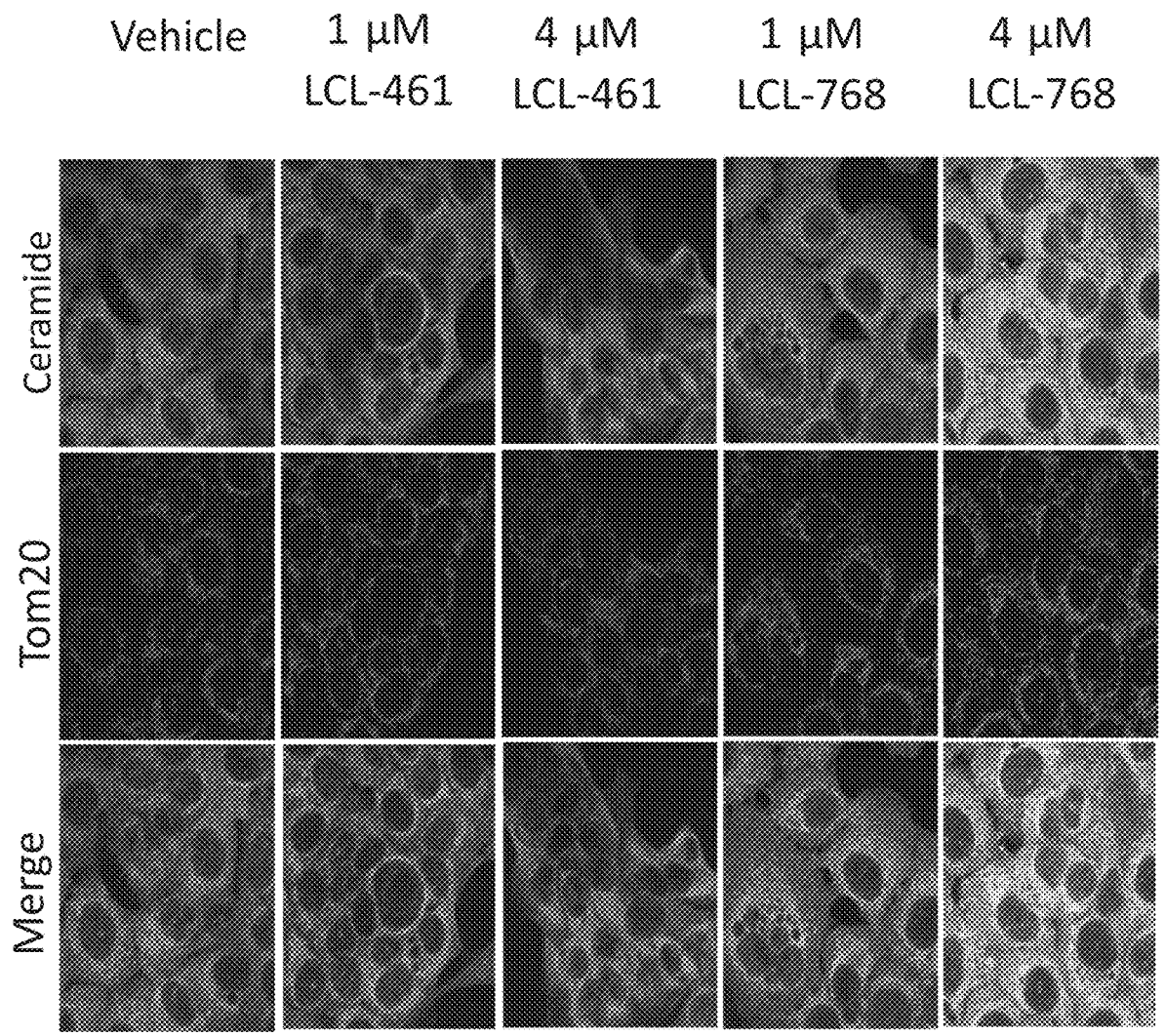
FIG. 4 is a series of confocal microscopy images of cells treated with 1 micromolar (1 µM) or 4 µM concentrations of a pyridinium-substituted ceramide-based compound (LCL-461), the selenite conjugated salt of a pyridinium-substituted ceramide-based compound (LCL-768), or vehicle for 1.5 hours and labeled for ceramide (top row), mitochondria (middle row) or both (bottom row).
Figure 5:
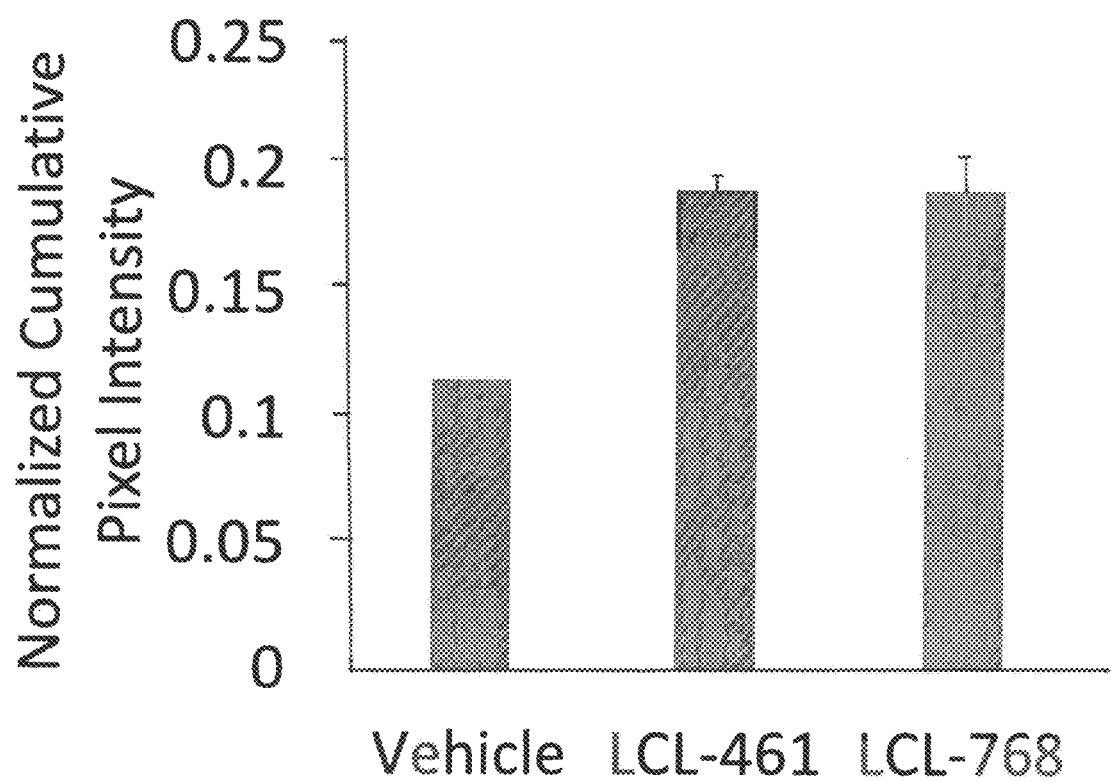
FIG. 5 is a graph showing levels of light chain 3B-II (LC3B-II) in head and neck squamous cell carcinoma (HNSCC-1A) cells incubated with 4 micromolar (µM) concentrations of a pyridinium-substituted ceramide-based compound (LCL-461), the selenite conjugated salt of a pyridinium ceramide-based compound (LCL-768), or vehicle for 1.5 hours. LC3B-II levels were measured via Western blotting. Image-processing software was used to quantify the band intensity from the blots.
Figure 6:
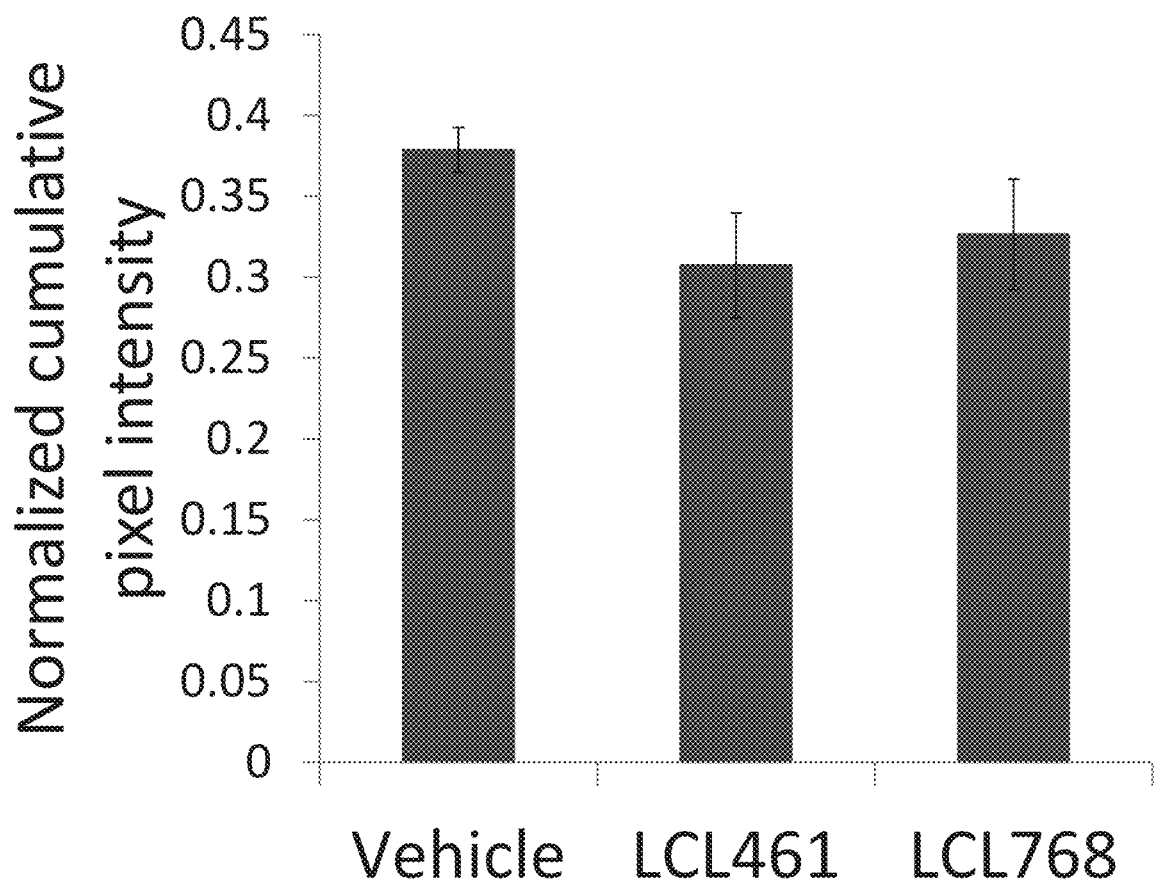
FIG. 6 is a graph showing levels of aconitase 2 (ACO2) (reported as normalized cumulative pixel intensity) in head and neck squamous cell carcinoma (HNSCC-1A) cells incubated with 4 micromolar (µM) concentrations of a pyridinium-substituted ceramide-based compound (LCL-461), the selenite conjugated salt of a pyridinium-substituted ceramide-based compound (LCL-768), or vehicle for 48 hours. ACO2 levels were measured via Western blotting. Image-processing software was used to quantify the band intensity from the blots.
Figure 7:
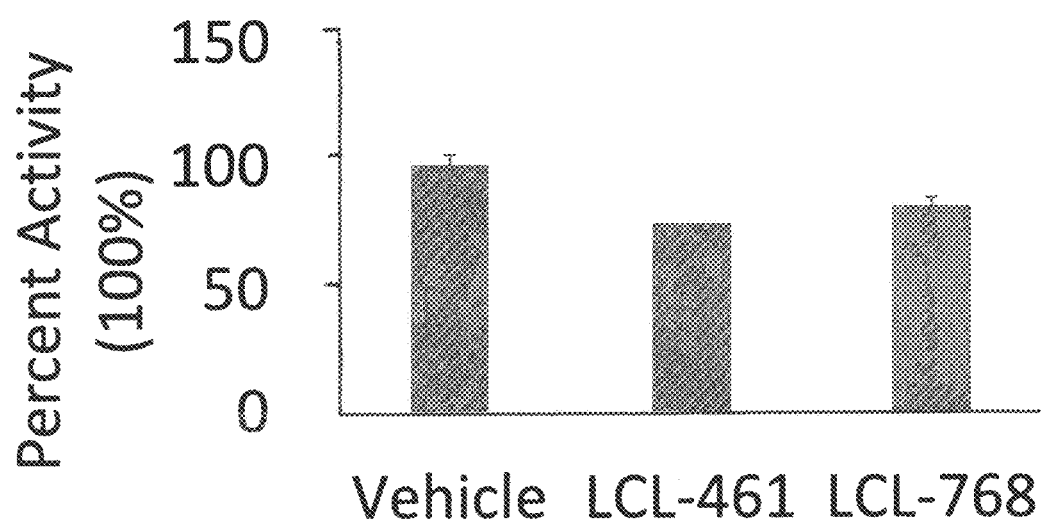
FIG. 7 is a graph showing adenosine triphosphate (ATP) activity in head and neck squamous cell carcinoma (HNSCC-1A) cells incubated with 4 micromolar (µM) concentrations of a pyridinium-substituted ceramide-based compound (LCL-461), the selenite conjugated salt of a pyridinium-substituted ceramide-based compound (LCL-768), or vehicle for 48 hours. ATP levels in the samples were measured, and all samples were normalized to a standard curve and then to vehicle activity.

Exposure of HNSCC-IA cells to low concentrations of LCL-768 (1 μM) showed significant increase in colocalization of CerS1 and mitochondrial protein Tom20 (see FIGS. 3A and 3B), suggesting a selenite-stress response. Exposure of HNSCC-1A cells to either of two concentrations (1 μM or 4 μM) of LCL-768 showed increased colocalization of ceramide and Tom20 compared to cells treated with both vehicle and LCL-461 at both concentrations (see FIG. 4), suggesting that LCL-461 does not cause a strong selenite-stress response. Short-term (1.5 hours) exposure to 4 μM LCL-461 or LCL-768 promotes autophagy as measured by increased LC3B-II levels. See FIG. 5. Longer-term (48 hours) exposure to 4 μM LCL-461 and LCL-768 promotes lethal mitophagy, as measured by decreased levels of ACO2 and ATP compared to vehicle. See FIGS. 6 and 7.

Figure 8A:
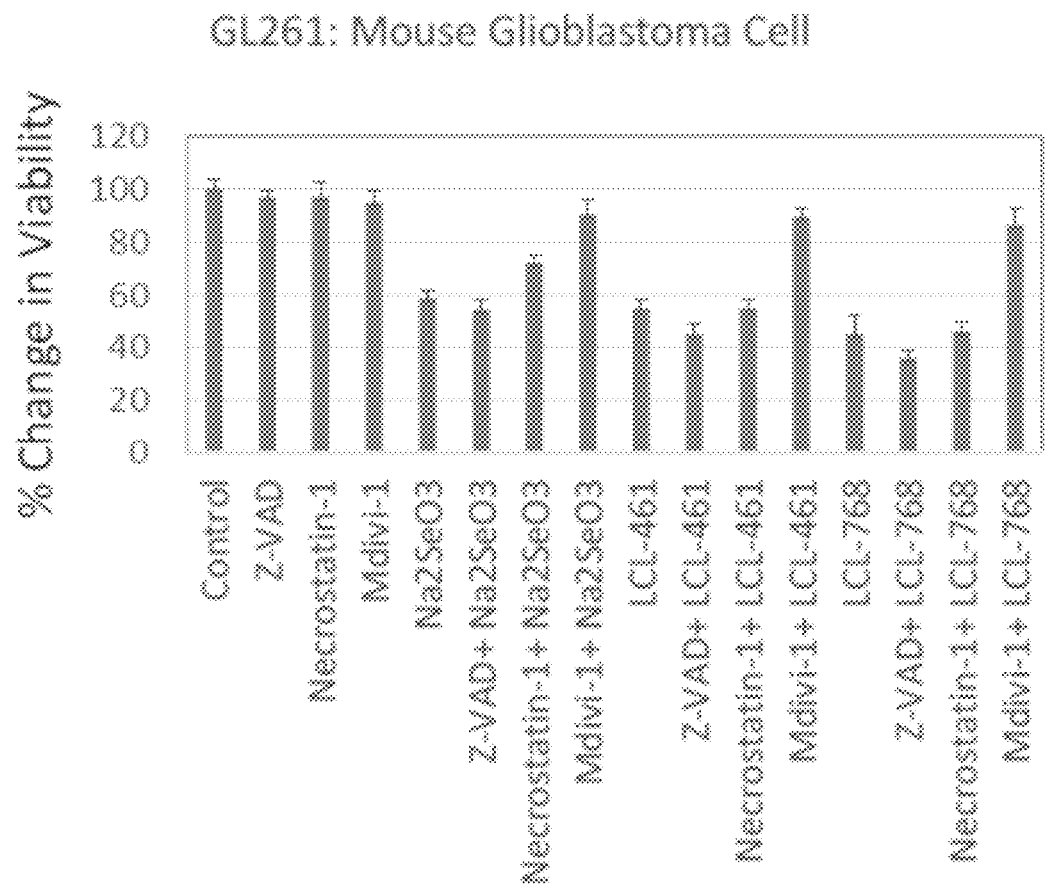
FIG. 8A is a graph showing cell viability (measured as percent (%) viability) determined via 3-(4,5-dimethylthiazol-2-yl)-2,5-dimethyltetrazolium bromide (MTT) assay for murine glioblastoma (GL261) cells treated for 24 hours with 5 micromolar (µM) LCL-768, one of the presently disclosed sphingolipid-based selenium (SPL-BSe) compounds, as compared to cells treated for 24 hours with a sphingolipid-based compound (LCL-461, 5 µM)) that is not conjugated to selenite anion or 5 µM sodium selenite (SoSe, $Na_2SeO_3$). Cell viability was also measured after 2 hour pretreatment of the cells with 5 µM pan caspase inhibitor Z-VAD, 5 µM RIP inhibitor Necrostatin-1, or 5 µM dynamin-related GTPase (DRP1) and dynamin 1 (Dnm1) inhibitor Mdivi-1, alone or in combination with the sodium selenite, LCL-461 or LCL-768 treatment.
Figure 8B:
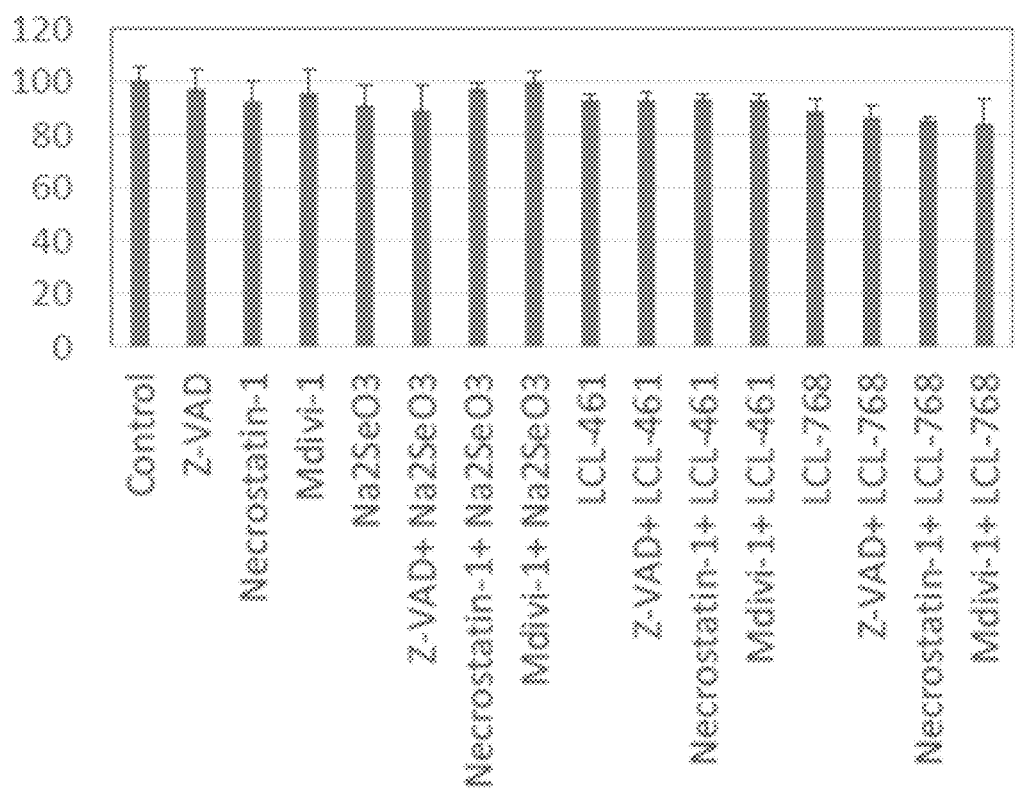
FIG. 8B is a graph showing cell viability (measured as percent (%) viability) determined via 3-(4,5-dimethylthiazol-2-yl)-2,5-dimethyltetrazolium bromide (MTT) assay for normal murine astrocytes treated for 24 hours with 5 micromolar (µM) LCL-768, one of the presently disclosed sphingolipid-based selenium (SPL-BSe) compounds, as compared to cells treated for 24 hours with a sphingolipid-based compound (LCL461, 5 µM) that is not conjugated to selenite anion or 5 µM sodium selenite (SoSe, $Na_2SeO_3$). Cell viability was also measured after 2 hour pretreatment of the cells with 5 µM pan caspase inhibitor Z-VAD, 5 µM RIP inhibitor Necrostatin-1, or 5 µM dynamin-related GTPase (DRP1) and dynamin 1 (Dnm1) inhibitor Mdivi-1, alone or in combination with the sodium selenite, LCL-461 or LCL-768 treatment.
Figure 9A:
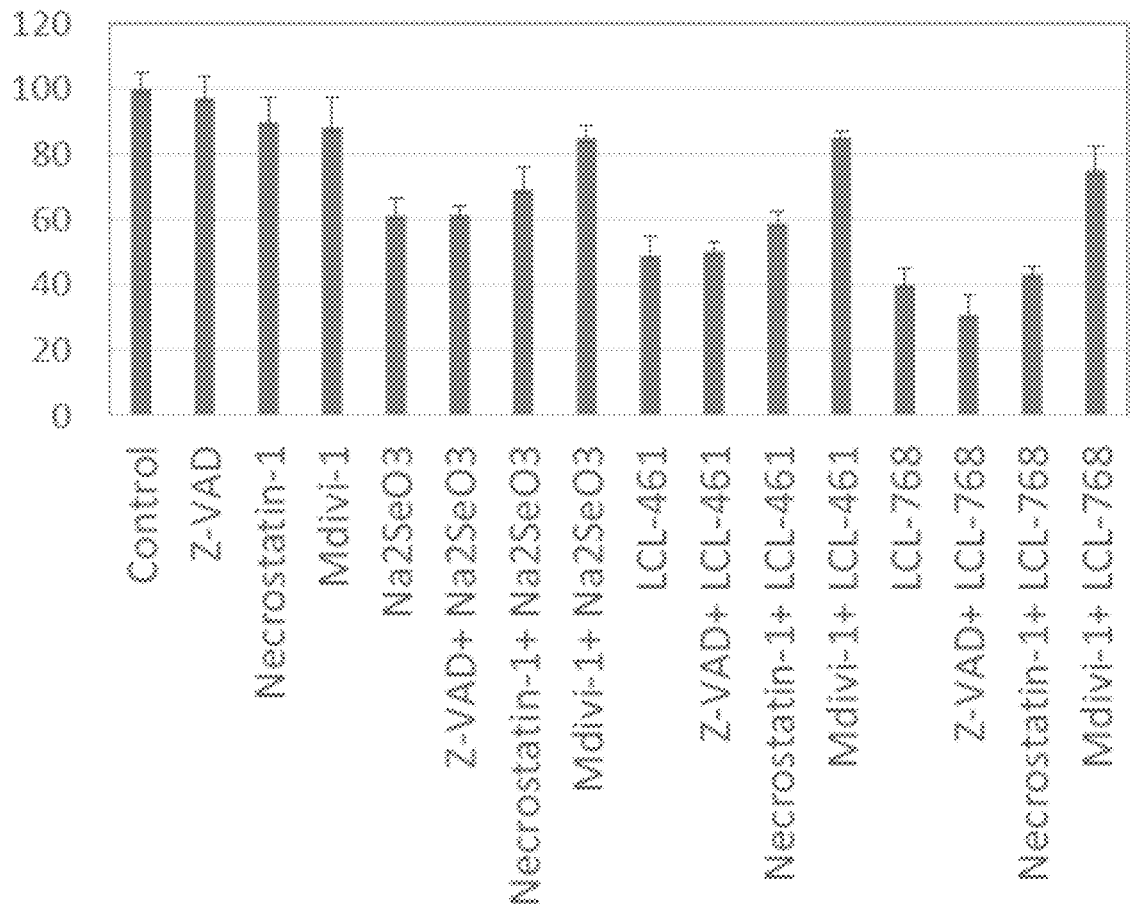
FIG. 9A is a graph showing cell viability (measured as percent (%) viability) determined via 3-(4,5-dimethylthiazol-2-yl)-2,5-dimethyltetrazolium bromide (MTT) assay for U118 (MGMT unmethylated, P53 Mu, PTEN Mu, EGRF+) human glioblastoma cells treated for 24 hours with 5 micromolar (5 µM) LCL-768, one of the presently disclosed sphingolipid-based selenium (SPL-BSe) compounds, as compared to cells treated for 24 hours with a sphingolipid-based compound (LCL-461, 5 µM)) that is not conjugated to selenite anion or 5 µM sodium selenite ($Na_2SeO_3$). Cell viability was also measured after 2 hour pretreatment with 5 µM pan caspase inhibitor Z-VAD, 5 µM RIP inhibitor Necrostatin-1, or 5 µM dynamin-related GTPase (DRP1) and dynamin 1 (Dnm1) inhibitor Mdivi-1, alone or in combination with sodium selenite, LCL-461 or LCL-768 treatment.
Figure 9B:
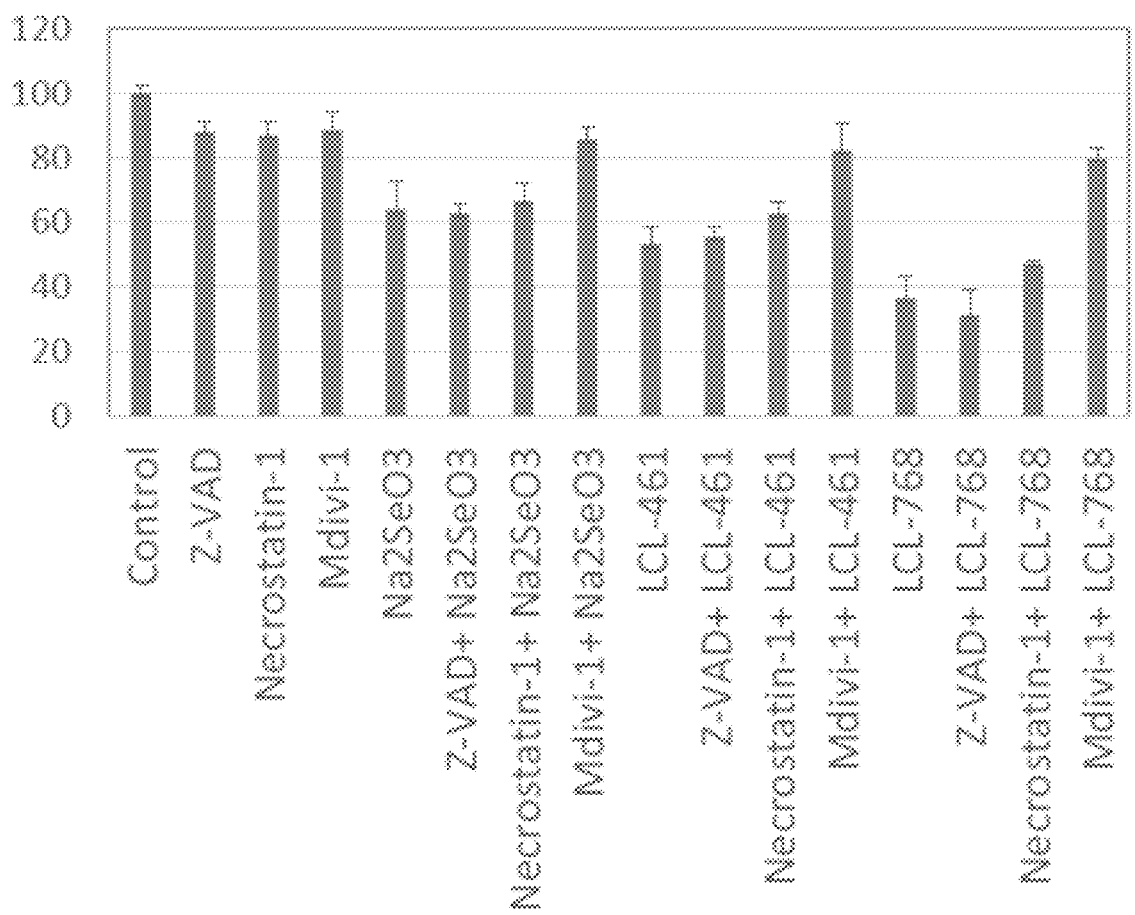
FIG. 9B is a graph showing cell viability (measured as percent (%) viability) determined via 3-(4,5-dimethylthiazol-2-yl)-2,5-dimethyltetrazolium bromide (MTT) assay for U87MG (MGMT methylated/deficient, P53 Wt, PTEN Mu, EGRF+) human glioblastoma cells treated for 24 hours with 5 micromolar (5 µM) LCL-768, one of the presently disclosed sphingolipid-based selenium (SPL-BSe) compounds, as compared to cells treated for 24 hours with a sphingolipid-based compound (LCL-461, 5 µM) that is not conjugated to selenite anion or 5 µM sodium selenite ($Na_2SeO_3$). Cell viability was also measured after 2 hour pretreatment of the cells with 5 µM pan caspase inhibitor Z-VAD, 5 µM RIP inhibitor Necrostatin-1, or 5 µM dynamin-related GTPase (DRP1) and dynamin 1 (Dnm1) inhibitor Mdivi-1, alone or in combination with sodium selenite, LCL-461 or LCL-768 treatment.
Figure 9C:
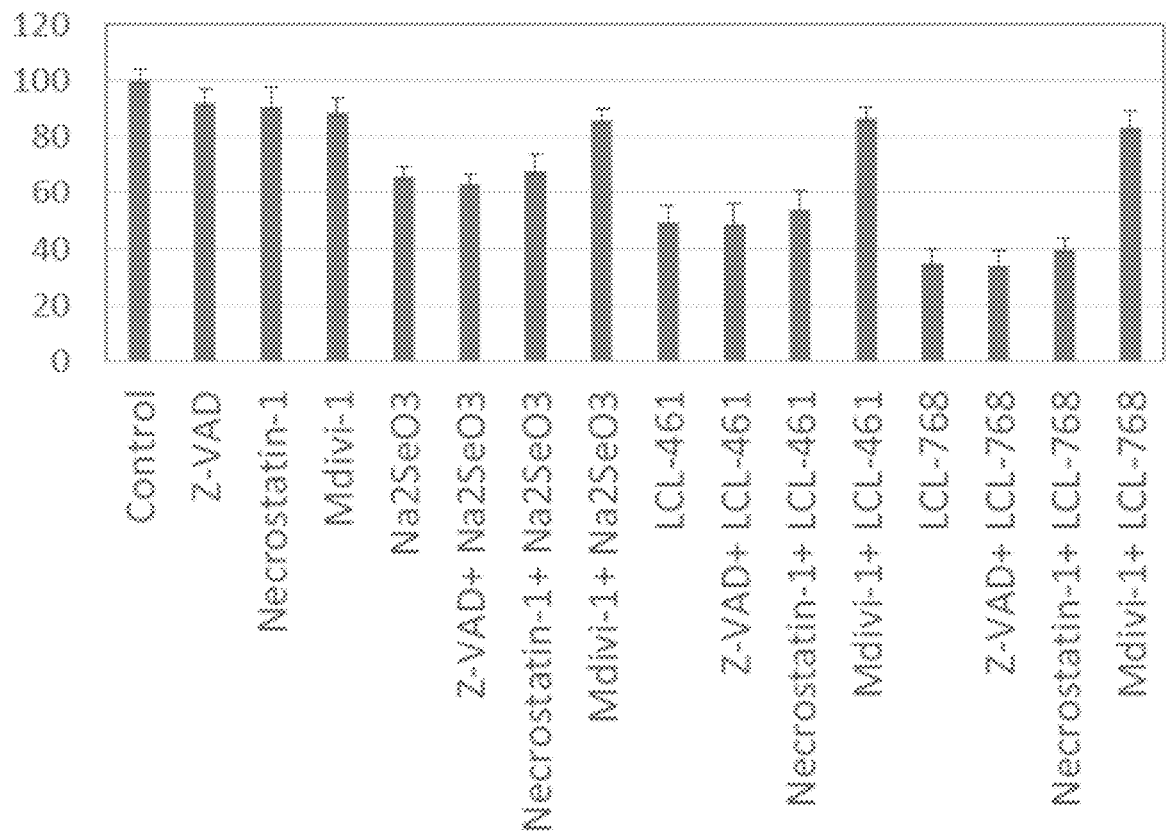
FIG. 9C is a graph showing cell viability (measured as percent (%) viability) determined via 3-(4,5-dimethylthiazol-2-yl)-2,5-dimethyltetrazolium bromide (MTT) assay for 43RG32 28 24 (MGMT unmethylated, P53 status:270 Phen>Cys, PTEN Wt, No EGRF) temozolamide resistant human glioblastoma cells treated for 24 hours with 5 micromolar (5 µM) LCL-768, one of the presently disclosed sphingolipid-based selenium (SPL-BSe) compounds, as compared to cells treated for 24 hours with a sphingolipid-based compound (LCL-461, 5 µM) that is not conjugated to selenite anion or 5 µM sodium selenite (SoSe, Na$_2$SeO$_3$). Cell viability was also measured after 2 hour pretreatment of the cells with 5 µM pan caspase inhibitor Z-VAD, 5 µM RIP inhibitor Necrostatin-1, or 5 µM dynamin-related GTPase (DRP1) and dynamin 1 (Dnm1) inhibitor Mdivi-1, alone or in combination with sodium selenite, LCL-461 or LCL768 treatment.
Figure 9D:
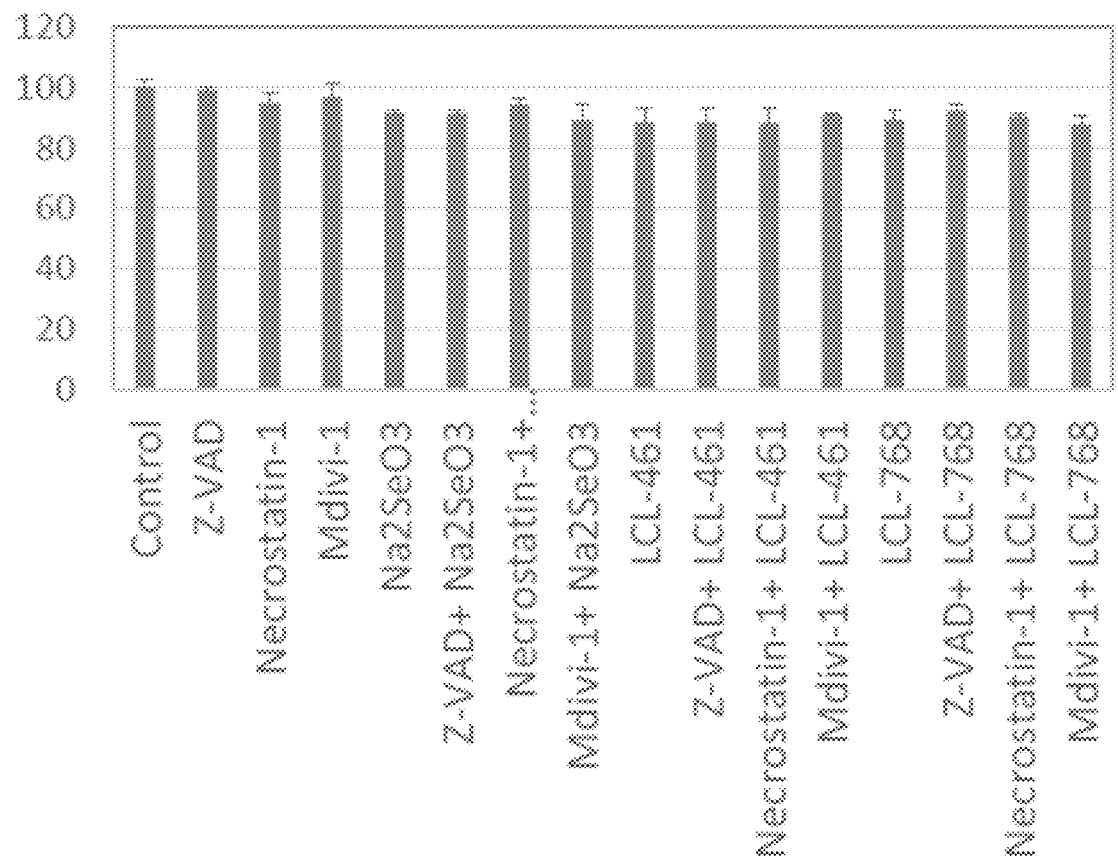
FIG. 9D is a graph showing cell viability (measured as percent (%) viability) determined via 3-(4,5-dimethylthi-azol-2-yl)-2,5-dimethyltetrazolium bromide (MTT) assay for normal human astrocyte (HA) cells treated for 24 hours with 5 micromolar (5 µM) LCL-768, one of the presently disclosed sphingolipid-based selenium (SPL-BSe) compounds, as compared to cells treated for 24 hours with a sphingolipid-based compound (LCL-461, 5 µM) that is not conjugated to selenite anion or 5 µM sodium selenite (SoSe, Na$_2$SeO$_3$). Cell viability was also measured after 2 hour pretreatment of the cells with 5 µM pan caspase inhibitor Z-VAD, 5 µM RIP inhibitor Necrostatin-1, or 5 µM dynamin-related GTPase (DRP1) and dynamin 1 (Dnm1) inhibitor Mdivi-1, alone or in combination with sodium selenite, LCL-461 or LCL-768 treatment.

As shown in FIGS. 8A and 8B, 24 hour treatment with exogenous LCL-768 induced autophagic cell death in mouse glioblastoma cells at a higher level than either LCL-461 or sodium selenite, while cell death was not induced by the compounds in mouse normal astrocytes isolated from mouse brain. Cell viability was also measured in the cells after 2 hour pretreatment with Z-VAD (a pan caspase inhibitor), necrostatin-1 (a specific RIP1 inhibitor that inhibits TNF-α induced necroptosis), or Mdivi-1 (a selective cell-permeable inhibitor of mitochondrial division DRP1 (dynamin-related GTPase) and mitochondrial division Dynamin 1 (Dnm1)). 24 hour treatment with exogenous LCL-768 also induced autophagic cell death in human glioblastoma cells compared to LCL-461 or sodium selenite. See FIGS. 9A-9C. Cell death was not induced by the compounds in human normal astrocytes. See FIG. 9D.

Figure 10:
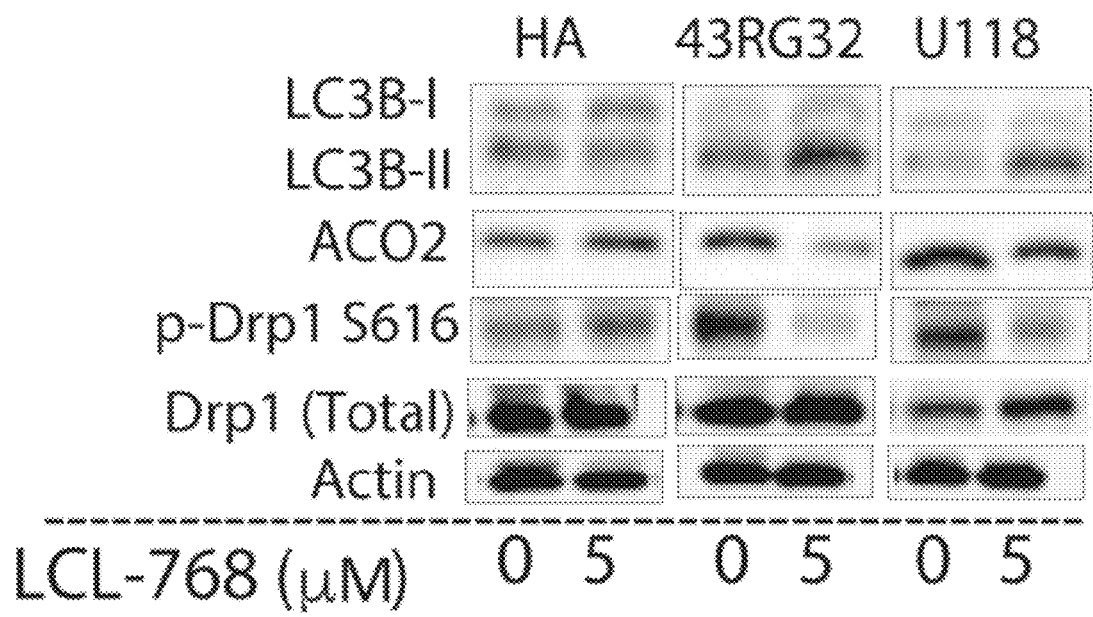
FIG. 10 is a composite gel image of Western blot analysis of extracts from non-cancerous human astrocytes (HA), 43RG32 and U118 cells treated with 0 micromolar (0 µM) or 5 µM LCL-768. The effects of LCL-768 on LC3-II activation, aconitase 2 (ACO2) degradation, and dynamin-related GTPase (Drp1) dephosphorylation at 3616 were measured as markers of mitophagy (n=3). The results show that LCL-768 induces mitophagy in non-cancerous HA.
Figure 11:
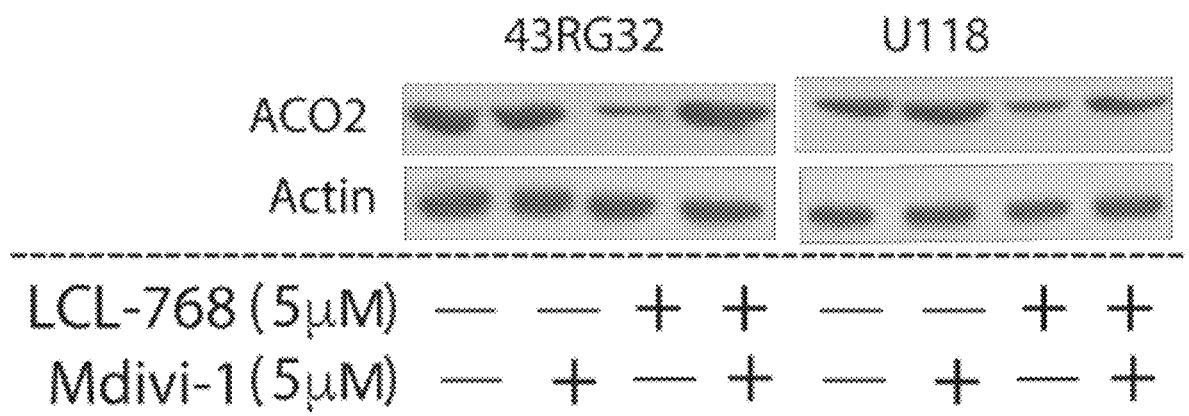
FIG. 11 is a composite gel image showing the effects of Mdivi-1-mediated inhibition of Drp1 on LCL-768-induced mitophagy were detected by Western blotting to measure the degradation of aconitase 2 (ACO2). 43RG32 and U118 glioblastoma cells were treated with (+) or without (−) 5 micromolar (5 µM) LCL-768 and with (+) or without (−) the Drp1 inhibitor Mdivi-1. Actin was used as a loading control (n=3). The results show that inhibition of dynamin-related GTPase (Drp1) by Mdivi-1 prevents LCL-768-mediated mitophagy.

Induction of mitophagy in response to LCL-768 was also confirmed by Western blotting using extracts isolated from non-cancerous human astrocytes (HA), 43RG32 and U118 cells. The results of the Western blotting revealed that LCL-768 induced LC-3B-II activation (autophagy marker) and ACO2 degradation (mitochondrial matrix protein degradation due to mitophagy) in 43RG32 and U118, but not HA cells. See FIG. 10. Inhibition of Drp1-mediated mitophagy by Mdivi-1 almost completely prevented LCL768-mediated ACO2 degradation in 43RG32 and U118 cells. See FIG. 11. Overall, these data suggest that pharmacologic restoring of C18-ceramide using LCL-461 and, more significantly, with LCL-768, results in GB cell death via LC3/Drp1 activation and mitophagy, leading to mitochondrial matrix protein ACO2 degradation.

Figure 12A:
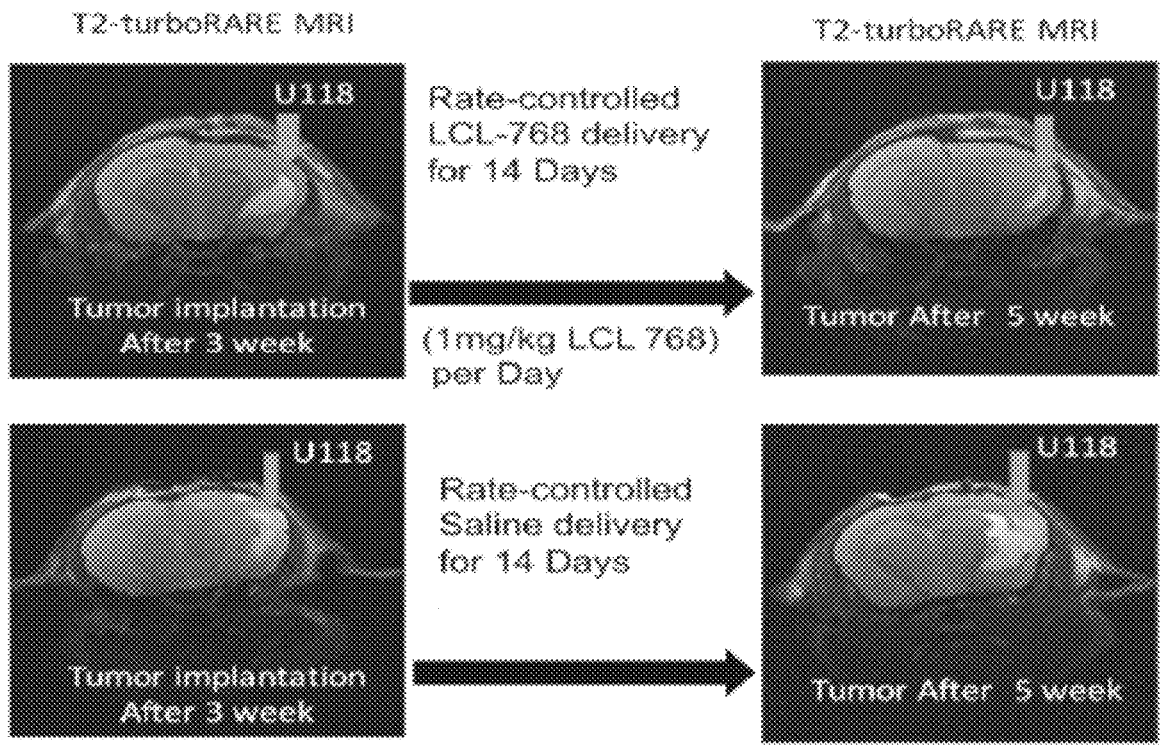
FIG. 12A is a set of representative magnetic resonance imaging (MRI) images of an orthotopic glioblastoma (GB) U118-xenograft-derived tumor in female severe combined immunodeficiency (SCID) mice undergoing treatment with LCL-768 (1 milligram per kilogram body weight per day (mg/kg/day); top two images) or vehicle (saline; bottom two images). The images on the left were taken three weeks after tumor implantation and the images on the right were taken five weeks after implantation (including 14 days of treatment with LCL-768 or vehicle). The area of the tumor is marked with the arrow labels U1118.
Figure 12B:
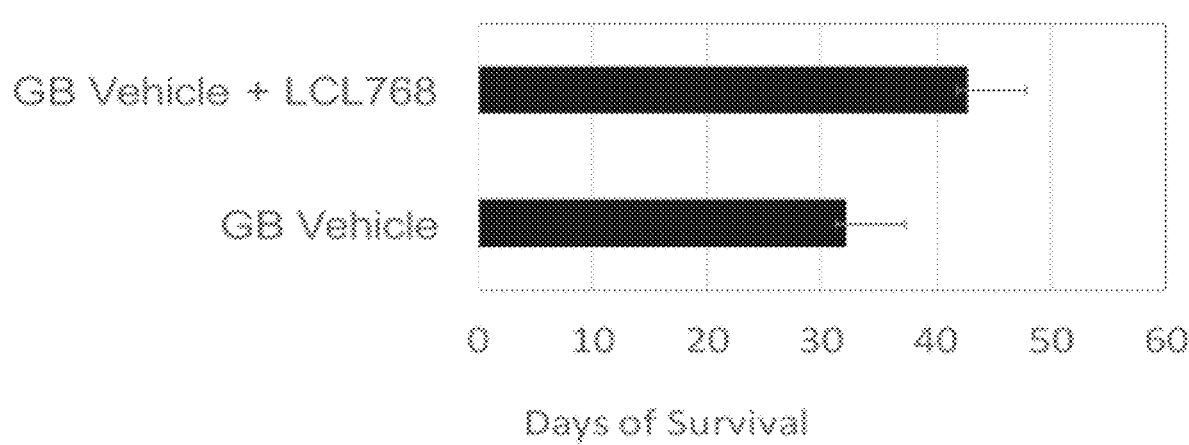
FIG. 12B is a graph showing the number of days of survival post treatment for groups (n=6) of female severe combined immunodeficiency (SCID) mice implanted with an orthotopic glioblastoma (GB) U118-xenograft-derived tumor treated with either 1 milligram per kilogram per day LCL-768 or vehicle (saline) for 14 days.

To determine the in vivo roles of LCL-768 in suppressing GB tumor growth, an orthotopic GB U118-xenograft-derived tumor was generated in the brains of female severe combined immunodeficiency (SCID) mice. The mice were treated with LCL-768 using an osmotic pump sold under the tradename ALZET™ (DURECT Corporation, Cupertino, California, United States of America) to release the drug in the tumors directly in the brain at 1 mg/kg/day for 14 days. Vehicle-treated mice were used as controls. The brain tumors were monitored by magnetic resonance imaging (MRI). The data showed that LCL-768 treatment remarkably reduced tumor growth in the brain compared to controls. See FIG. 12A. Treatment also increased the survival of mice about 10 days post-treatment, See FIG. 12B. These data suggest that LCL-768 suppresses orthotopic GB growth in mice and improves survival (even after treatment is stopped).

Example 3

Additional Anticancer Effects of SP-BSes

Figure 13A:
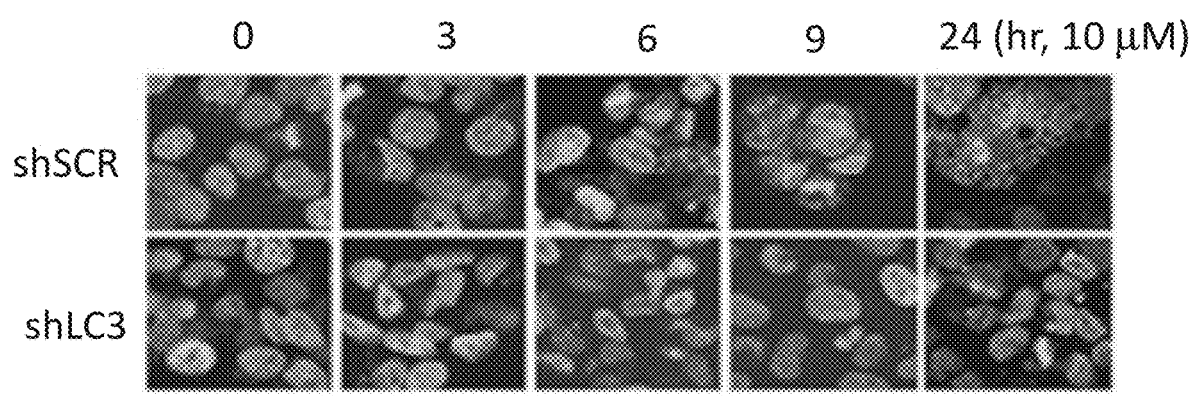
FIG. 13A is a series of fluorescence microscopy images showing the effects of LCL-768 (10 micromolar (µM)) on mitophagy induction. The effects were measured using a autophagy detection kit sold under the tradename CYTO-ID™ (Enzo Life Sciences, Inc., Farmingdale, New York, United States of America) using immunofluorescence (green signal indicates mitophagy) at (from left to right) 0, 3, 6, 9, or 24 hours in human head and neck squamous cell carcinoma (HNSCC) cells (UM-SCC-1A cells) stably transfected with short hairpin RNA (shRNA) against LC3B (shLC3, bottom row) or with control shRNA (shSCR, top row).
Figure 13B:
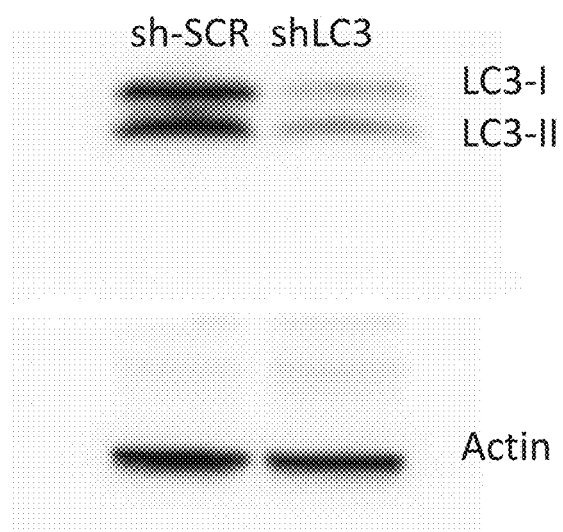
FIG. 13B is an image of an immunoblot showing the effects on LC3-I and LC3-II in human head and neck squamous cell carcinoma (HNSCC) cells (UM-SCC-1A cells) stably transfected with short hairpin RNA (shRNA) against LC3B (shLC3, right) compared to the same cells stably transfected with control shRNA (shSCR, left).
Figure 13C:
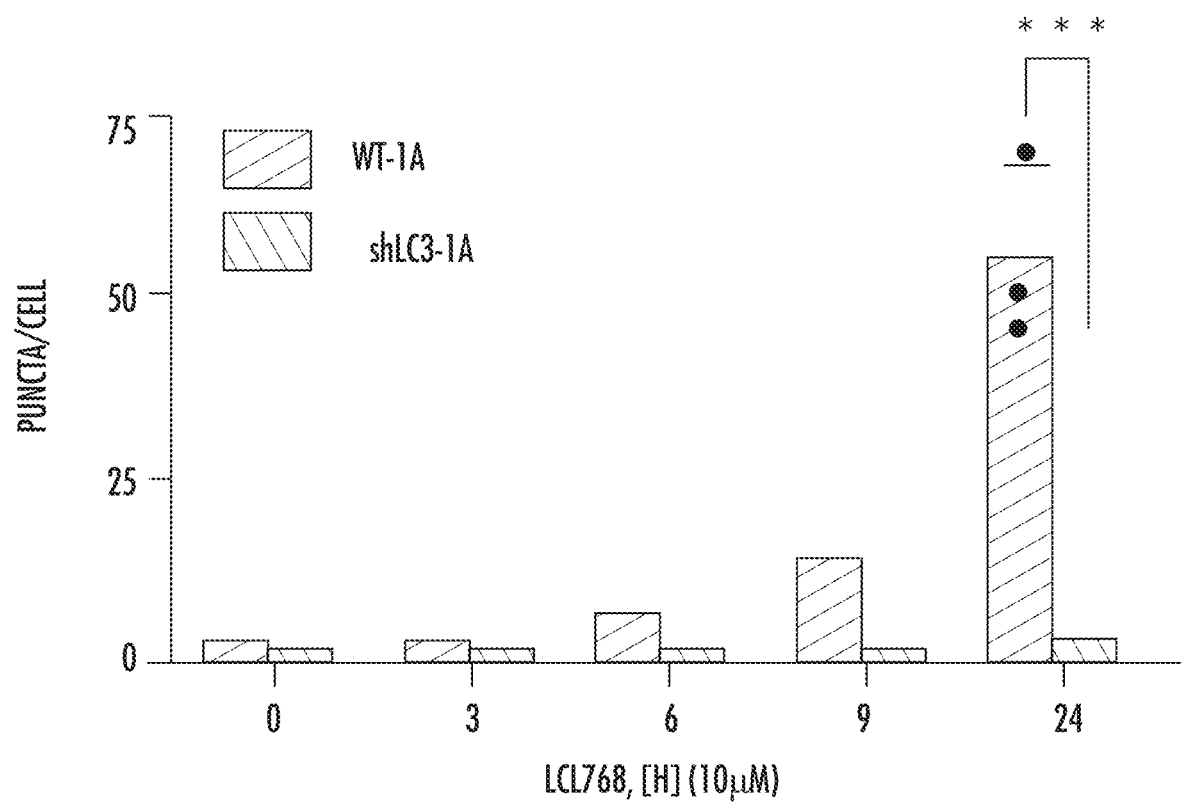
FIG. 13C is a graph showing the quantification of results shown in FIG. 13A.
Figure 13D:
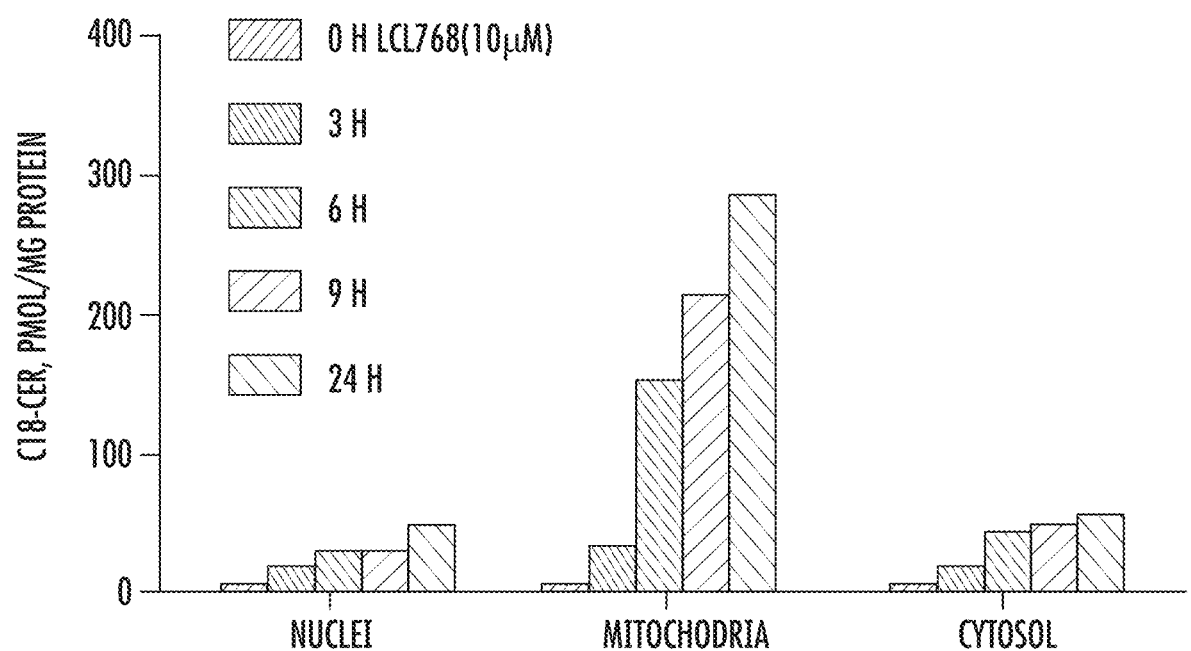
FIG. 13D is a graph showing the subcellular accumulation of LCL-768 (10 micromolar (µM)) after 0, 3, 6, 9, or 24 hours in the nucleus, mitochondria and cytoplasm of human head and neck squamous cell carcinoma (HNSCC) cells (UM-SCC-1A cells) as measured by mass spectrometry/lipidomics after differential centrifugation.

The effects of LCL-768 on mitophagy induction in UM-SCC-IA cells transfected stably with the shRNA against LC3B (shLC3) was studied and compared to controls (UM-SCC-1A cells transfected with a control shRNA, shSCR). LCL-768 (10 µM) at 6, 9 and 24 hours highly induced mitophagy in shSCR-controls, and knockdown of LC3 almost completely prevented mitophagy induction. See FIGS. 13A-13C. The subcellular accumulation of LCL-768 was studied in the same cells. Nucleus, mitochondria and cytoplasm in LCL-768-treated cells were isolated by differential centrifugation and LCL-768 accumulation was measured by mass spectrometry. The data showed that LCL-768 largely accumulated in the mitochondria at 6-24 hours in UM-SCC-1A cells, See FIG. 13D. Thus, these studies further support mitochondrial accumulation and efficacy of LCL-768 in inducing mitophagy in UM-SCC-1A cells.

Figure 14A:
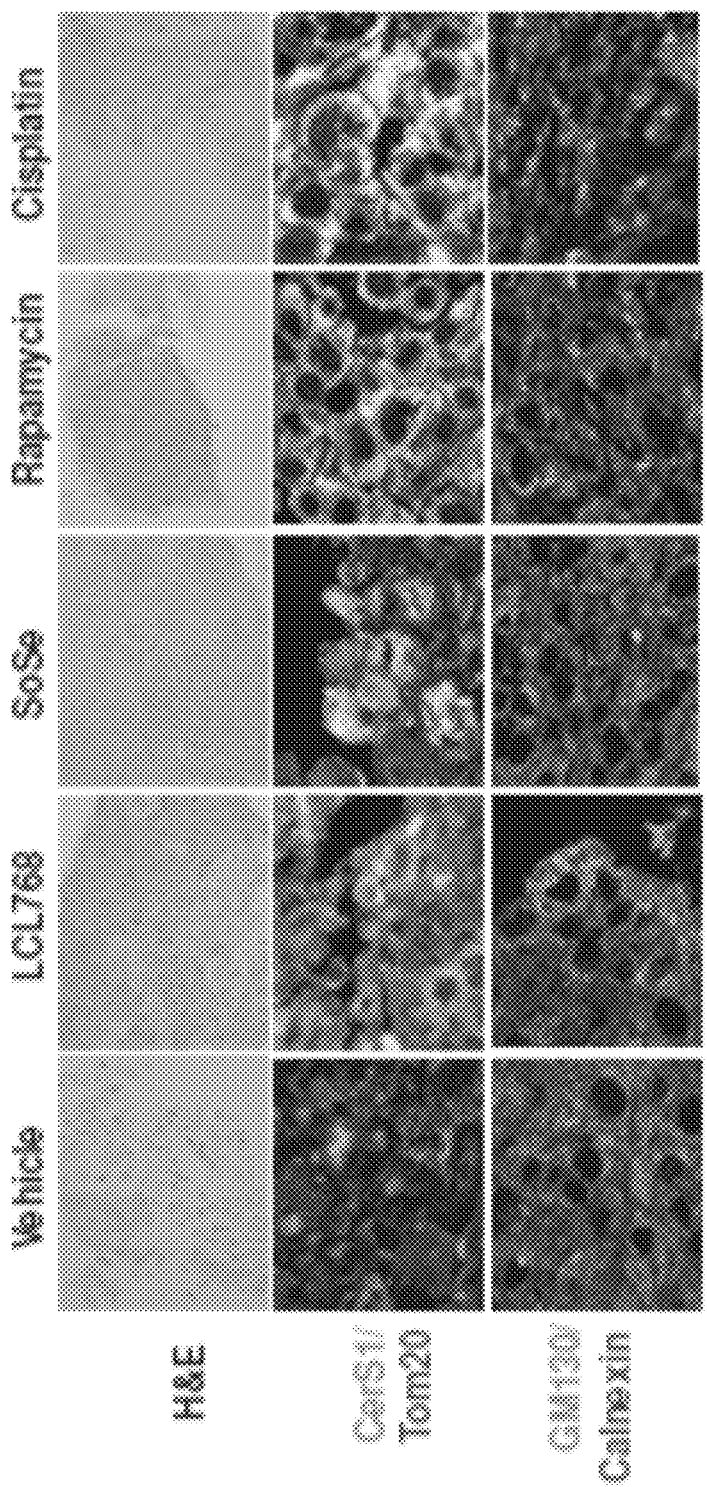
FIG. 14A is a series of microscopy images showing the H&E staining (top row) and fluorescence imaging of the co-localization of translocase of outer mitochondrial membrane 20 (Tom20) and CerS1 (as a measure of mitophagy, middle row) in two-dimensional (2D) organoids developed from a patient with head and neck squamous cell carcinoma (HNSCC) in response to treatment with vehicle, LCL-768, sodium selenite (SoSe), rapamycin, or cisplatin ex vivo. Co-localization of cis-Golgi matrix protein 130 kDa (GM130) and Calnexin was used as a negative control (bottom row).
Figure 14B:
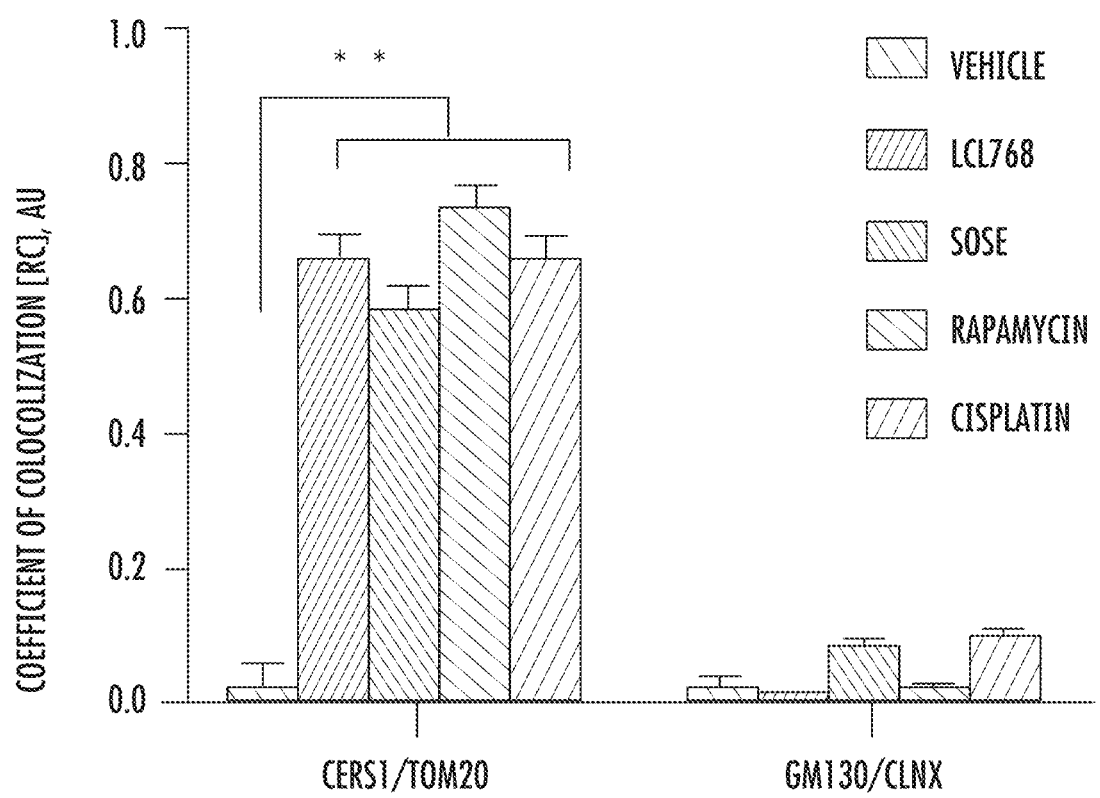
FIG. 14B is a graph showing the quantification of colocalization of Tom20 and CerS1 from the treated two-dimensional (2D) organoids described for FIG. 14A.
Figure 14C:
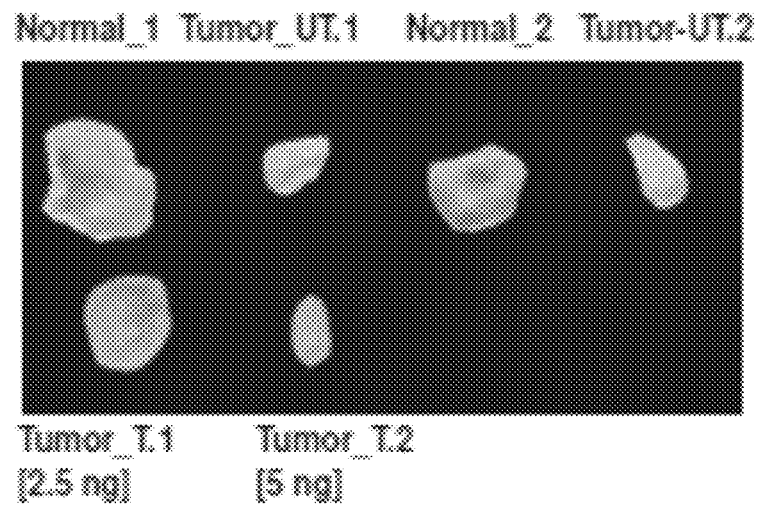
FIG. 14C is an image showing the H&E staining of LCL-768-treated two-dimensional (2D) organoids containing HNSCC tumor or non-cancerous adjacent head and neck tissue (normal).
Figure 14D:
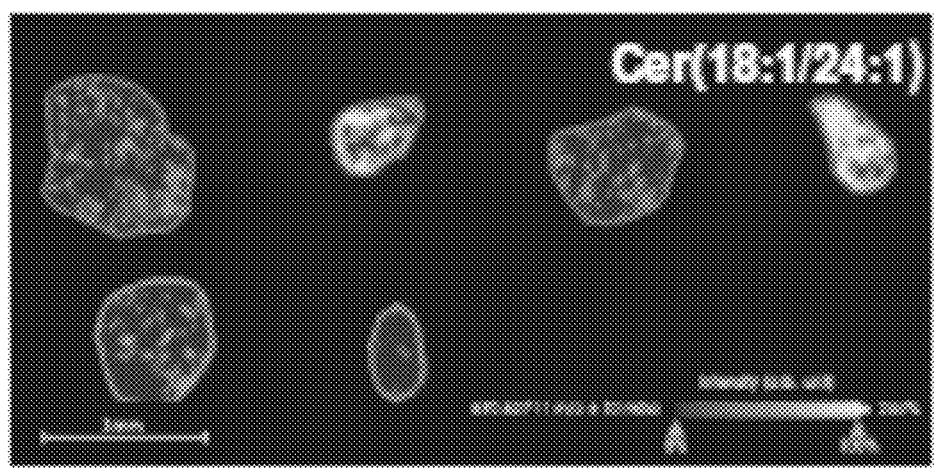
FIG. 14D is an image showing the effects of LCL-768 treatment on the two-dimensional (2D) organoids described for FIG. 14C as measured using MALDI-Imaging technology.
Figure 14E:
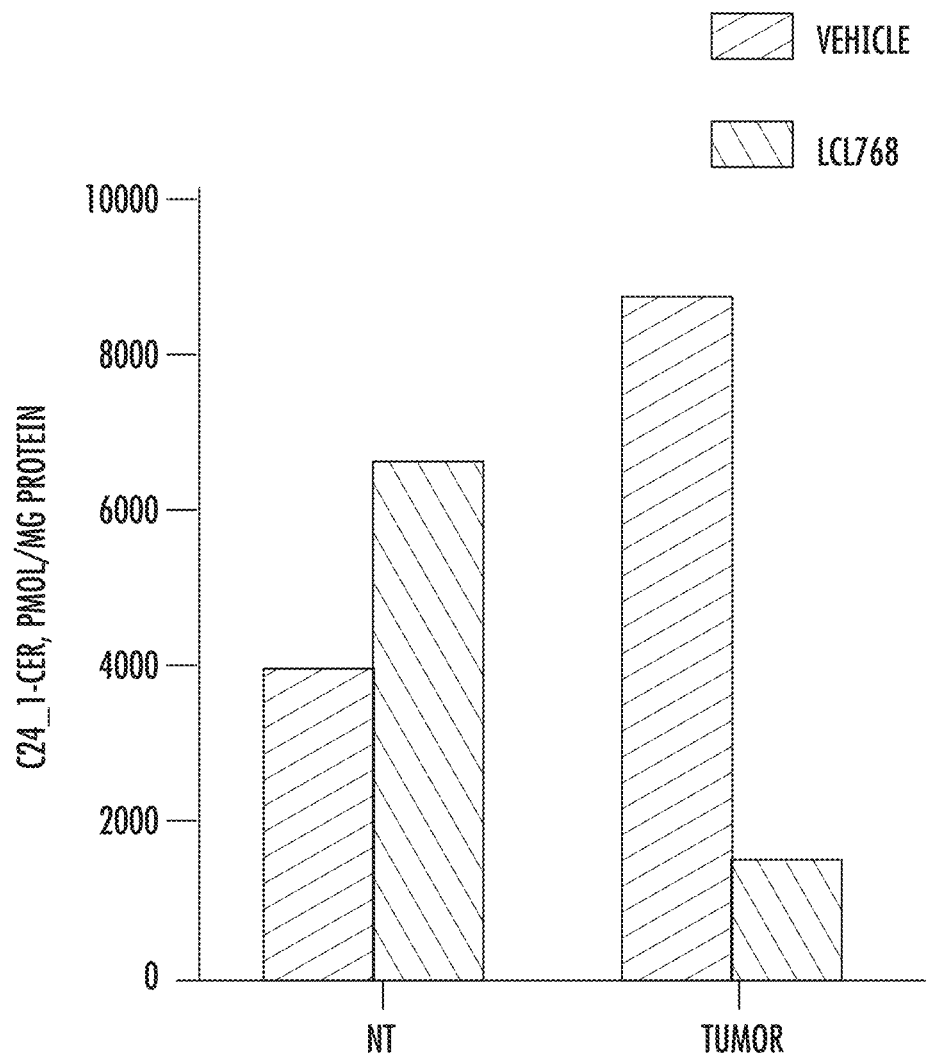
FIG. 14E is a graph showing the effects of LCL-768 treatment on C24 ceramide production in two-dimensional organoids derived from human head and neck squamous cell carcinoma tissue (Tumor) or non-tumor tissue (NT). As a control, the organoids were also treated with vehicle as a control.

To validate the clinical relevance of the activation of mitophagy, 2D organoids[4] were developed using tumor tissues obtained from a patient with HNSCC. See FIG. 14A. Ex vivo treatment of the organoids with LCL-768, SoSe, rapamycin, and cisplatin induced mitophagy compared to vehicle-treated controls in HNSCC organoids as determined by immunofluorescence studies based on the co-localization of CerS1 and Tom20. See FIG. 14B. The co-localization of GM130/Calnexin was used as a control. These treatments did not affect mitophagy induction in non-cancerous adjacent tissue organoids obtained from the same patient. The effects of ex vivo treatment of HNSCC organoids with LCL-768 on endogenous $C_{24}$-ceramide was studied using matrix-assisted laser desorption/ionization (MALDI)-Imaging.[5] C24 has been shown to promote tumor proliferation. LCL-768 decreased $C_{24}$-ceramide in HNSCC organoids compared to controls. See FIGS. 14C-14E.

Figure 15A:
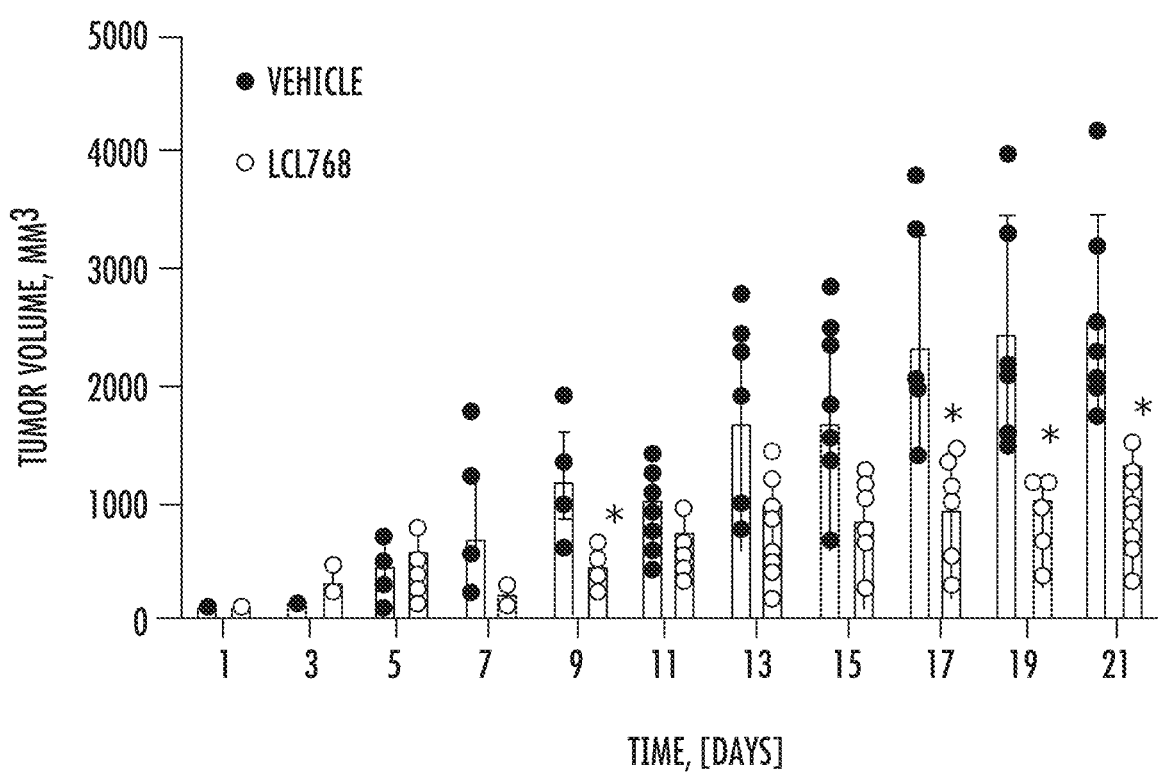
FIG. 15A is a graph showing the effects of LCL-768 (10 milligrams per kilogram (mg/kg)) on human head and neck squamous cell carcinoma (HNSCC) cell (UM-SCC-IA)-derived xenografts grown in the flanks of severe combined immunodeficiency (SCID) mice were measured at 21 days (after injections of the drug intraperitoneal (P)/every other day). Tumor volume (cubic millimeters (mm$^3$)) is provided for both LCL-76B mice and mice treated with vehicle as a control.
Figure 15B:
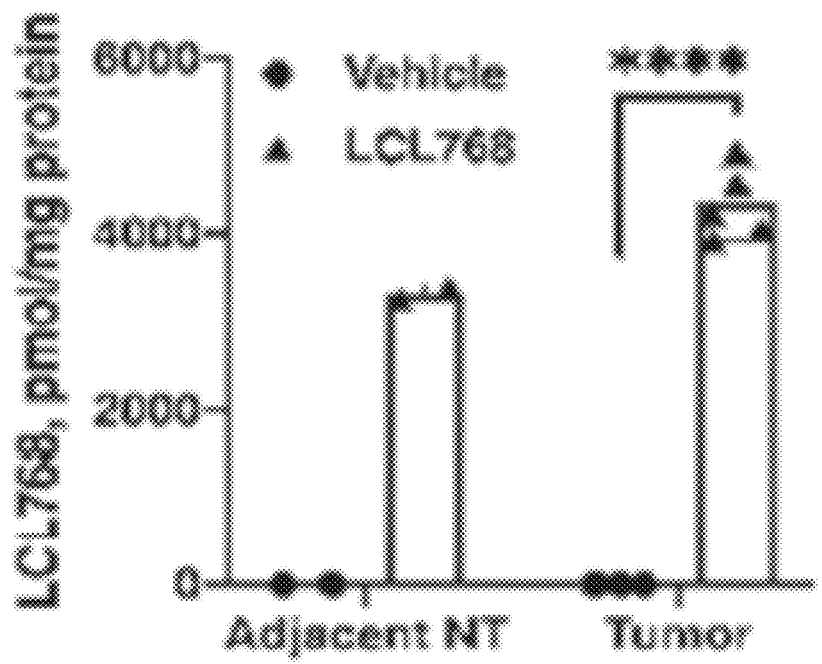
FIG. 15B is a graph showing the accumulation of LCL-768 (measured as picomoles per milligram protein (pmol/mg protein) in xenograft-derived tumors and adjacent non-tumorigenic tissues (NT) at day 21 of the treatment regimen described for FIG. 15A as measured by mass spectrometry.
Figure 15C:
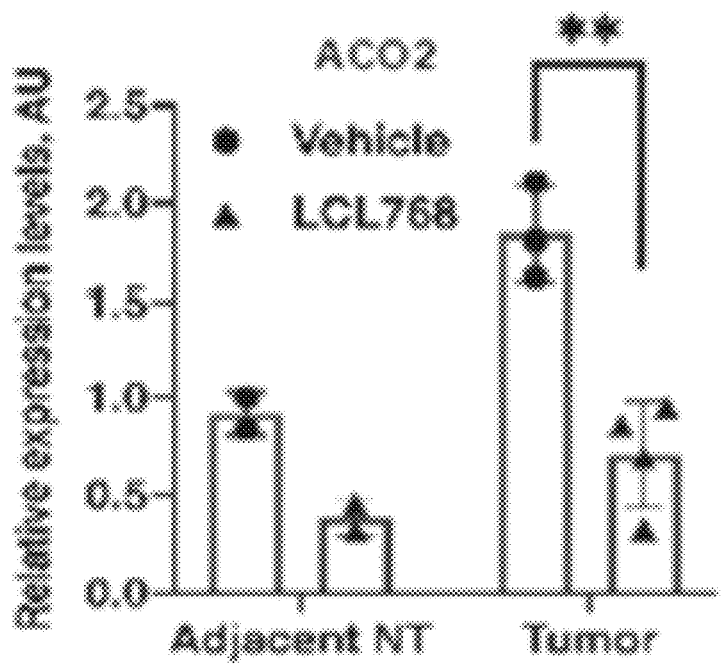
FIG. 15C is a graph showing the effects of LCL-768 on mitophagy induction in xenograft-derived tumors (Tumor) and adjacent non-tumorigenic tissues (adjacent NT) measured by decreased aconitase 2 (ACO2).
Figure 15D:
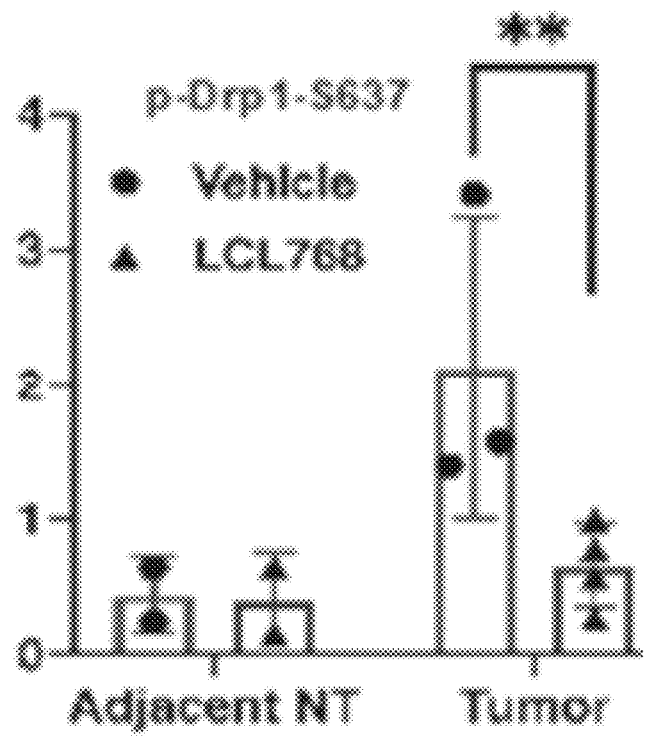
FIG. 15D is a graph showing the effects of LCL-768 on mitophagy in xenograft-derived tumors (Tumor) and adjacent non-tumorigenic tissues (adjacent NT) measured by activation of Drp1, via reduced P-S637, measured by Western blotting (normalized to GAPDH).
Figure 15E:
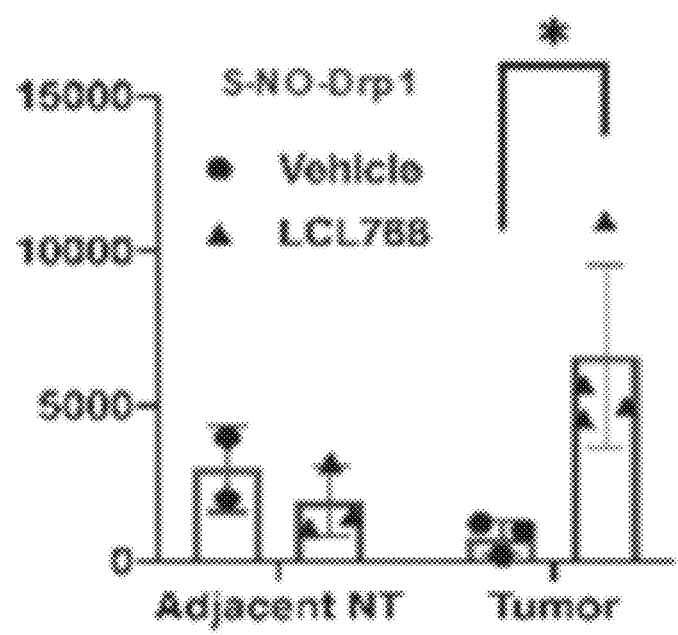
FIG. 15E is a graph showing the effects of LCL-768 on mitophagy in xenograft-derived tumors (Tumor) and adjacent non-tumorigenic tissues (adjacent NT) measured by increased S-nitrosylation of Drp1, S-NO-Drp1, examined via IP and Western blotting using anti-NO-Cys and ant-Drp1 antibodies (normalized to total protein). *P<0.05, n=12.

The maximum tolerated does (MTD) of LCL-768 was determined as 10 mg/kg in SCID mice. Treatment of mice containing UM-SCC-1A-xenografts with LCL-768 inhibited tumor growth significantly compared to vehicle-treated mice. See FIG. 15A. Inhibition of tumor growth by LCL-768 was also consistent with its higher tumor accumulation and induction of mitophagy. See FIGS. 15B-15E. Thus, the present studies support the efficacy of LCL-768 on the inhibition of HNSCC tumor growth and mitophagy induction in vivo.

1.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A selenium-containing conjugate having the formula:

$$\left( \begin{array}{c} R_1 \diagdown A \diagup \hspace{-2pt} = \hspace{-2pt} \diagdown \hspace{-4pt} \left(\hspace{-4pt}\right)_{\hspace{-4pt}m} \hspace{-4pt} \diagdown R_3 \\ R_2 \diagdown N \diagup Y' \diagdown \left(\hspace{-4pt}\right)_n \hspace{-4pt} R_4 \\ \underset{O}{\|} \end{array} \right)_z \cdot (SeO_3^{-2})_y,$$

wherein:
n is an integer from 3 to 21;
m is an integer from 1 to 5;
z is 1 or 2;
y is an integer of 1 or more;
A is —CH(OH)—;
Y' is selected from —CH$_2$—, —NH—, and —CH(OH)—;
$R_1$ is —CH$_2$OH;
$R_2$ is selected from —H and $C_1$-$C_6$ alkyl; and
each $R_6$ and $R_7$ is independently —C$_1$-C$_5$ alkyl,
wherein $R_3$ and $R_4$ are each selected from —H and N-heterocycle, subject to the proviso that at least one of $R_3$ and $R_4$ is N-heterocycle, wherein the N-heterocycle is pyridinium or substituted pyridinium.

2. The selenium-containing conjugate of claim 1, wherein $R_2$ is —H.

3. The selenium-containing conjugate of claim 1 having the formula:

$$\left( \begin{array}{c} \overset{OH}{\vdots} \\ HO \diagdown \diagup \diagdown \diagup = \diagdown \left(\hspace{-4pt}\right)_{\hspace{-4pt}m} \hspace{-4pt} \diagdown R_3 \\ H \diagdown N \diagup \left(\hspace{-4pt}\right)_n \hspace{-4pt} R_4 \\ \underset{O}{\|} \end{array} \right)_2 \cdot (SeO_3^{-2}),$$

wherein:
m is an integer from 1 to 5;
n is an integer from 1 to 21; and
$R_3$ and $R_4$ are each selected from —H and N-heterocycle, subject to the proviso that when $R_3$ is —H, $R_4$ is N-heterocycle and when $R_3$ is N-heterocycle, $R_4$ is —H.

4. The selenium-containing conjugate of claim 3, wherein m is 5, n is 13, $R_3$ is —H, and $R_4$ is pyridinium or wherein m is 1, n is 15, $R_3$ is pyridinium, and $R_4$ is —H.

5. The selenium-containing conjugate of claim 1 having the formula:

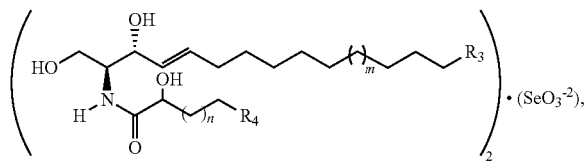

wherein:
m is an integer from 1 to 5;
n is an integer from 3 to 21; and
$R_3$ and $R_4$ are each selected from —H and N-heterocycle, subject to the proviso that when $R_3$ is —H, $R_4$ is N-heterocycle and when $R_3$ is N-heterocycle, $R_4$ is —H.

6. The selenium-containing conjugate of claim 5, wherein n is an integer from 3 to 15.

7. A pharmaceutical formulation, comprising a pharmaceutically acceptable carrier and the selenium-containing conjugate of claim 1.

8. A method of treating cancer in a subject in need thereof, the method comprising the step of administering orally or by injection to the subject the selenium-containing conjugate of claim 1 and a pharmaceutically acceptable carrier.

9. The method of claim 8, wherein the treatment provides increased reduction in tumor cell load or reduced off-target toxicity compared to a treatment with a non-conjugated mixture of a selenium-containing compound and a sphingolipid-based therapeutic agent.

10. The method of claim 8, wherein the method provides effective use of a lower concentration of a selenite anion than a method wherein the selenite anion is not administered as part of an ionic conjugate with a cationic ceramide analog.

11. The method of claim 8, wherein the cancer is a head and neck cancer or a brain cancer.

12. The selenium-containing conjugate of claim 1 that is D-erythro-16-(1'-pyridinium)-N-hexadecanoyl-sphingosine selenite or D-erythro-14-(1'-pyridinium)-N-octadecanoyl-sphingosine selenite.

13. The method according to claim 8, wherein the selenium-containing conjugate is D-erythro-6-(1'-pyridinium)-N-hexadecanoyl-sphingosine selenite or D-erythro-14-(1'-pyridinium)-N-octadecanoyl-sphingosine selenite.

14. The method according to claim 8, wherein said cancer is a glioblastoma.

* * * * *